(12) United States Patent
Kessler et al.

(10) Patent No.: US 11,504,001 B2
(45) Date of Patent: Nov. 22, 2022

(54) SURGERY 3D VISUALIZATION APPARATUS

(71) Applicant: Raytrx, LLC, Tulsa, OK (US)

(72) Inventors: David Kessler, New York, NY (US);
Michael H. Freeman, Tulsa, OK (US);
Mitchael C. Freeman, Tulsa, OK (US);
Simon Prosser, Tulsa, OK (US);
Jordan Boss, Tulsa, OK (US); Steven Yeager, Tulsa, OK (US)

(*) Notice: Subject to any disclaimer, the term of this patent is extended or adjusted under 35 U.S.C. 154(b) by 0 days.

(21) Appl. No.: 17/706,912

(22) Filed: Mar. 29, 2022

(65) Prior Publication Data
US 2022/0322936 A1    Oct. 13, 2022

Related U.S. Application Data

(60) Provisional application No. 63/168,353, filed on Mar. 31, 2021.

(51) Int. Cl.
*A61B 3/14* (2006.01)
*A61B 90/00* (2016.01)
*H04N 5/30* (2006.01)

(52) U.S. Cl.
CPC .............. *A61B 3/14* (2013.01); *A61B 90/361* (2016.02); *H04N 5/30* (2013.01); *A61B 2090/3614* (2016.02); *A61B 2090/3618* (2016.02); *H04N 2213/001* (2013.01)

(58) Field of Classification Search
CPC . A61B 3/14; A61B 90/361; A61B 2090/3614; A61B 2090/3618; H04N 5/30; H04N 2213/001
See application file for complete search history.

(56) References Cited

U.S. PATENT DOCUMENTS

| | | | | |
|---|---|---|---|---|
| 5,835,264 A * | 11/1998 | Tandler | .................. | G02B 21/22 348/57 |
| 5,997,141 A * | 12/1999 | Heacock | ............. | A61F 9/00821 606/4 |
| 2003/0071987 A1* | 4/2003 | Matsumura | ............ | G01B 11/24 356/124 |
| 2008/0174869 A1* | 7/2008 | Cathey | .................. | G02B 21/14 359/558 |
| 2010/0232016 A1* | 9/2010 | Landa | .................. | G02B 5/1814 359/466 |

(Continued)

OTHER PUBLICATIONS

Co-Pending utility U.S. Appl. No. 17/712,535 by David Kessler et al. entitled "Surgery 3D Visualization Apparatus" filed Apr. 4, 2022.

*Primary Examiner* — James M Pontius
(74) *Attorney, Agent, or Firm* — Howard & Howard Attorneys LLC

(57) ABSTRACT

An apparatus for obtaining an image of a retina has an optical relay that defines an optical path and is configured to relay an image of the iris along the optical path to a pupil; a shutter disposed at the pupil and configured to define at least a first shutter aperture for control of light transmission through the pupil position; a tube lens disposed to direct light from the shutter aperture to an image sensor; and a prismatic input port disposed between the shutter and the tube lens and configured to combine, onto the optical path, light from the relay with light conveyed along a second light path that is orthogonal to the optical path.

23 Claims, 31 Drawing Sheets

(56) References Cited

U.S. PATENT DOCUMENTS

| | | | | |
|---|---|---|---|---|
| 2013/0113892 | A1* | 5/2013 | Nakamaru | H04N 13/144 348/47 |
| 2013/0128223 | A1* | 5/2013 | Wood | A61B 1/0684 351/246 |
| 2013/0258462 | A1* | 10/2013 | May | G03B 17/565 359/464 |
| 2013/0307939 | A1* | 11/2013 | May | G03B 17/565 348/49 |
| 2022/0087525 | A1* | 3/2022 | Oki | A61B 3/112 |

* cited by examiner

SURGERY 3D VISUALIZATION APPARATUS

CROSS REFERENCE TO RELATED APPLICATIONS

This application claims the benefit of U.S. Provisional Application Ser. 63/168,353, entitled "SURGERY 3D VISUALIZATION APPARATUS", in the names of David Kessler, Ph.D., Michael H. Freeman, J. D., et al., filed on 31 Mar. 2021 and incorporated herein in its entirety.

FIELD OF THE DISCLOSURE

The present disclosure generally relates to optical apparatus for clinical and surgical use and more particularly to a system for acquisition and display in ophthalmology for visualization of patient retina and cornea under examination and treatment.

BACKGROUND

Continuing advances in medical treatment have been provided using improved systems for visualization, helping to support the medical practitioner with advanced functions and features that employ aspects of digital image acquisition, processing, and display. Handling image content in digital form, in turn, allows advanced surgical support systems to provide automated functions that include robotic procedural assistance, telemedicine applications, and application of Machine Learning (ML) and Artificial Intelligence (AI).

In many cases, digital image acquisition and visualization tools have been added to legacy systems that were designed for use with analog and some earlier electronic visualization tools, limiting the abilities of full digital applications. Such earlier systems provide some level of advancement, but often suffer from poor ergonomics and are not readily modified or adaptable for taking better advantage of digital processing and display capabilities.

Systems especially useful for ophthalmology present a particular challenge, due to factors including complexity of the optical path, space constraints, difficulties related to brightness, and disappointing resolution. Indirect ophthalmoscope techniques, widely used for eye examination and surgery, has taken some advantage of digital imaging tools, but remains a highly manual process that requires careful positioning of an objective lens very near the patient's cornea and at the proper angle relative to a light source, as well as accurate positioning of the practitioner for observation. These criteria require an expert surgeon or practitioner to operate. With problems such as low patient tolerance to bright light and the often-poor quality of the viewed image, indirect ophthalmoscopy remains a difficult procedure that can be inaccurate and may degrade the overall quality of retinal examination.

The stereomicroscope is a widely used tool in ophthalmology, particularly for intraocular surgery. Particular challenges for this device include the following:
 (i) need to image all portions of the eye in 3D, for both the cornea and the retina;
 (ii) need to switch easily from anterior to posterior imaging;
 (iii) need for systems where the components close to the patients are can be easily and expediently sterilized to reduce operation time and cost;
 (iv) requirements for patient safety during operation;
 (v) need for improved surgeon ergonomics;
 (vi) poor visibility of various features within the eye due to the limited aperture sizes of the 3D apertures;
 (vii) need for higher resolution for detection;
 (viii) need for wide angle visibility of the retina;
 (ix) image rectification;
 (x) need to reduce microscope size to reduce patient obscuration and to allow maneuverability of the microscope for orientation at different viewing angles;
 (xi) need to be able to readily switch from lower resolution 3D mode to a high-resolution monoscopic or mesoscopic viewing-mode;
 (xii) need to be able to use both in intra-vitreous illumination as well as external illumination.

Faced with these challenges, stereomicroscopy design has provided some solutions, but there is considerable room for improvement. It can be appreciated that there is a need for improved visualization apparatus and approaches for support of ophthalmoscopy and other functions used for detailed patient examination and treatment.

SUMMARY OF THE INVENTION

The Applicants address the problem of advancing the art of digital acquisition and visualization for examination and surgical applications. Acquired microscope and resulting still or video 2D and 3D images can be magnified by virtue of optical zoom, as described herein, and digital zoom together which provide the magnification in embodiments of the present disclosure.

With this object in mind, there is provided an ophthalmic stereomicroscopy apparatus comprising an apparatus for posterior ophthalmology work by obtaining an image of a retina comprising:
 (a) an optical relay that defines an optical path and is configured to relay an image of the iris along the optical path to a pupil;
 (b) a shutter disposed at the pupil and configured to define at least a first shutter aperture for control of light transmission through the pupil position;
 (c) a tube lens disposed to direct light from the shutter aperture to one or more image sensors;
 and
 (d) a prismatic input port disposed between the shutter and the tube lens and configured to combine, onto the optical path, light from the relay with light conveyed along a second light path that is orthogonal or extraneous to the optical path.

The apparatus can be compact and maneuverable, usable in surgery with the patient horizontally disposed or usable in the optometrist or ophthalmologist office environment for eye examination, with the patient vertically disposed (such as seated or standing).

The practitioner can switch from 3D mode to monoscopic mode for higher resolution and improved Signal-to-Noise Ratio (SNR). The practitioner can also change the degree of stereopsis and azimuth.

The practitioner can obtain 2D or 3D imagery while avoiding imperfections on the patient cornea or iris. The system allows both conventional illumination with an auxiliary illumination unit or with coaxial illumination.

The system can be used in combination with anterior segment ophthalmology wherein a cornea imaging system may use a combination of elements, or two systems can be mounted adjacently on a microscope turret, which are then selectable by the physician by mechanical or electronic means. The retina imaging attachment described herein can be used as a standalone imaging device, typically useful for office examination by the practitioner. When mounted as part of a larger imaging system, the retina imaging attachment can be mounted on a turret or other type of switching device and used to automate office examination imaging as well as for imaging during surgical procedures. Robotic actuators, not shown, can be used to position and increment the imaging attachment at different angles for more complete imaging content.

Unlike a slit-lamp or direct or indirect ophthalmoscopy examinations, which take place with the naked eyes of the physician, this method provides the added improvement of taking and presenting still or video images (collectively, "video") to record and, if needed, to use for subsequent examination.

DRAWINGS

DETAILED DESCRIPTION

Figure 1A:
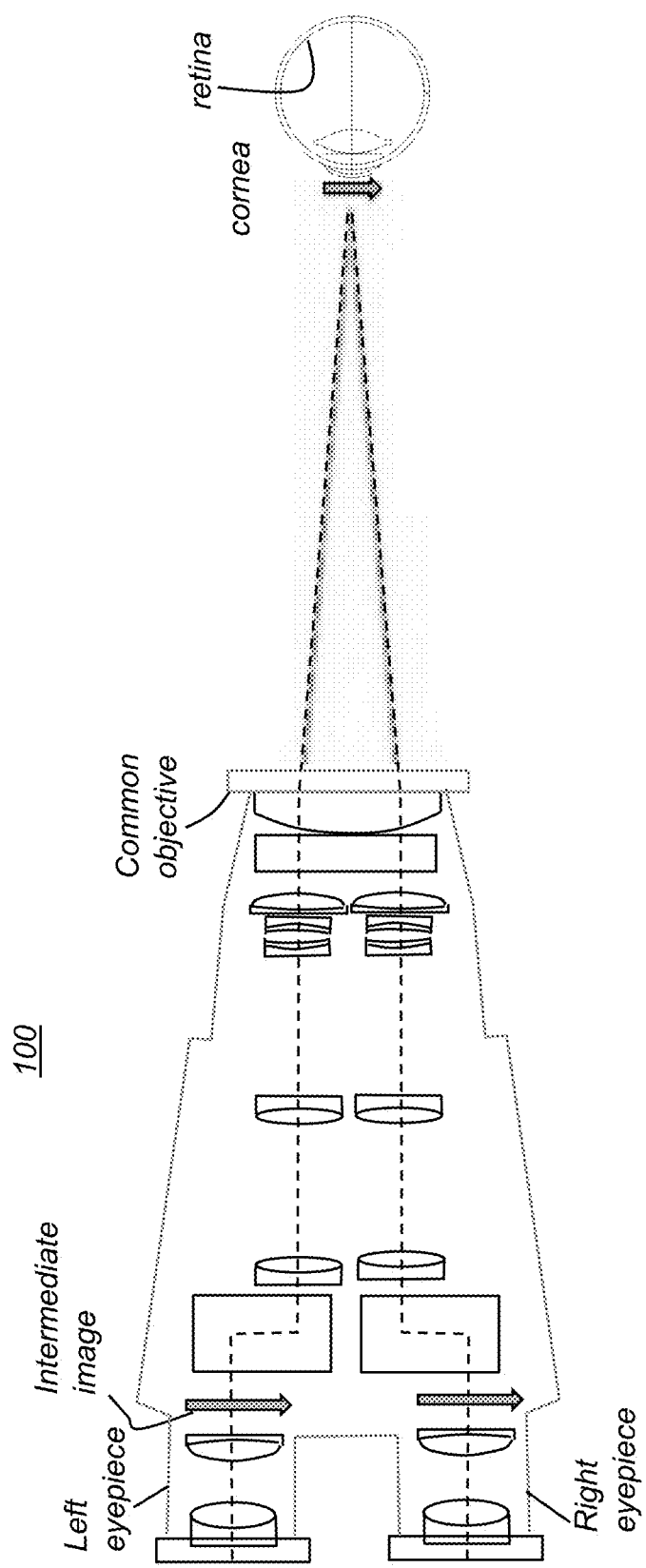
FIG. 1A is a schematic view showing basic components of a conventional 3D stereomicroscope.

The following is a detailed description of the preferred embodiments of the disclosure, reference being made to the drawings in which the same reference numerals identify the same elements of structure in each of the several figures.

Where they are used, the terms "first", "second", and so on, do not necessarily denote any ordinal, sequential, or priority relation, but are simply used to more clearly distinguish one element or set of elements from another, unless specified otherwise.

While the devices and methods have been described with a certain degree of particularity, it is to be noted that many modifications may be made in the details of the construction and the arrangement of the devices and components without departing from the spirit and scope of this disclosure. It is understood that the devices and methods are not limited to the embodiments set forth herein for purposes of exemplification. It will be apparent to one having ordinary skill in the art that the specific detail need not be employed to practice according to the present disclosure. In other instances, well-known materials or methods have not been described in detail in order to avoid obscuring the present disclosure.

Reference throughout this specification to "one embodiment," "an embodiment," "one example," or "an example" means that a particular feature, structure, or characteristic described in connection with the embodiment or example is included in at least one embodiment of the present disclosure. Thus, appearances of the phrases "in one embodiment," "in an embodiment," "one example," or "an example" in various places throughout this specification are not necessarily all referring to the same embodiment or example. Furthermore, the particular features, structures, or characteristics may be combined in any suitable combinations and/or sub-combinations in one or more embodiments or examples.

In the context of the present disclosure, the term "coupled" when referring to mechanical components is intended to indicate a mechanical association, connection, relation, or linking, between two or more components, such that the disposition of one component affects the spatial disposition of a component to which it is coupled. For mechanical coupling, two components need not be in direct contact, but can be linked through one or more intermediary components.

With particular respect to electronic signal content, several (or different) elements discussed herein and/or claimed are described as being "coupled," "in communication with," "integrated," or "configured to be in signal communication with" or a "system" or "subsystem" thereof. This terminology is intended to be non-limiting and, where appropriate, can be interpreted to include, without limitation, wired and wireless communication using any one or a plurality of a suitable protocols, as well as communication methods that are constantly maintained, are made on a periodic basis, and/or made or initiated on an as-needed basis.

As used herein, the term "energizable" relates to a device or set of components that perform an indicated function when energized, that is, upon receiving power and, optionally, upon receiving an enabling signal. The word "exemplary" is used herein to mean "serving as an example, instance, or illustration." Any aspect described herein as "exemplary" is not necessarily to be construed as preferred or advantageous over other aspects.

Some portions of embodiments in accordance with the present disclosure may be embodied as a system, an apparatus, a method, a computer program, hardware/software, and/or product, including encoded instructions on a transitory or non-transitory computer-readable storage medium. All of the systems and subsystems may exist, or portions of the systems and subsystems may exist to form the solution of the present disclosure. Accordingly, the apparatus of the present disclosure may take the form of an entirely hardware embodiment, an entirely software embodiment (including firmware, resident software, micro-code, etc.), or an embodiment combining software and hardware aspects that may all generally be referred to herein as a "unit," "module," or "system." Furthermore, the apparatus of the present disclosure may take the form of a computer program product embodied in any tangible media of expression having computer-usable program code embodied in the media. Any combination of one or more computer-usable or computer-readable media (or medium) may be utilized. For example, a random-access memory (RAM) device, a read-only memory (ROM) device, an erasable programmable read-only memory (EPROM or Flash memory) device, a portable compact disc read-only memory (CDROM), an optical storage device, and a magnetic storage device. Computer program code for carrying out operations of the present disclosure may be written in any combination of one or more programming languages. Further, the intelligence in the main logic circuitry may be software, firmware, or hardware, and can be microcontroller based or included in a state machine. The apparatus of the present disclosure may be a combination of the above intelligence and memory, and this can exist in a central processing unit or a multiple of chips including a central graphics chip. The computer portion of the apparatus of the present disclosure may also include a model view controller (MVC) or "model controller."

Attachment Structure

FIG. 1A is a schematic view showing basic components of a conventional 3D stereomicroscope 100. A stereo eyepiece pair provides binocular visibility to features of the cornea. Stereomicroscope 100 has an objective lens for viewing the cornea in 3D, typically at a distance of 175 to 200 mm. Two optical systems are used, which may incorporate zoom optics, one for each eye of the surgeon. The arrows indicate typical object and image orientation. In this system, eyepieces are used which limit the positioning of the microscope with respect to the patient, as the surgeon often needs to reposition, sometimes in strained posture, in order to do so. Some of the more recent microscopes have replaced the eyepieces with cameras (not shown); however, the large microscope size is still prevalent.

Figure 1B:
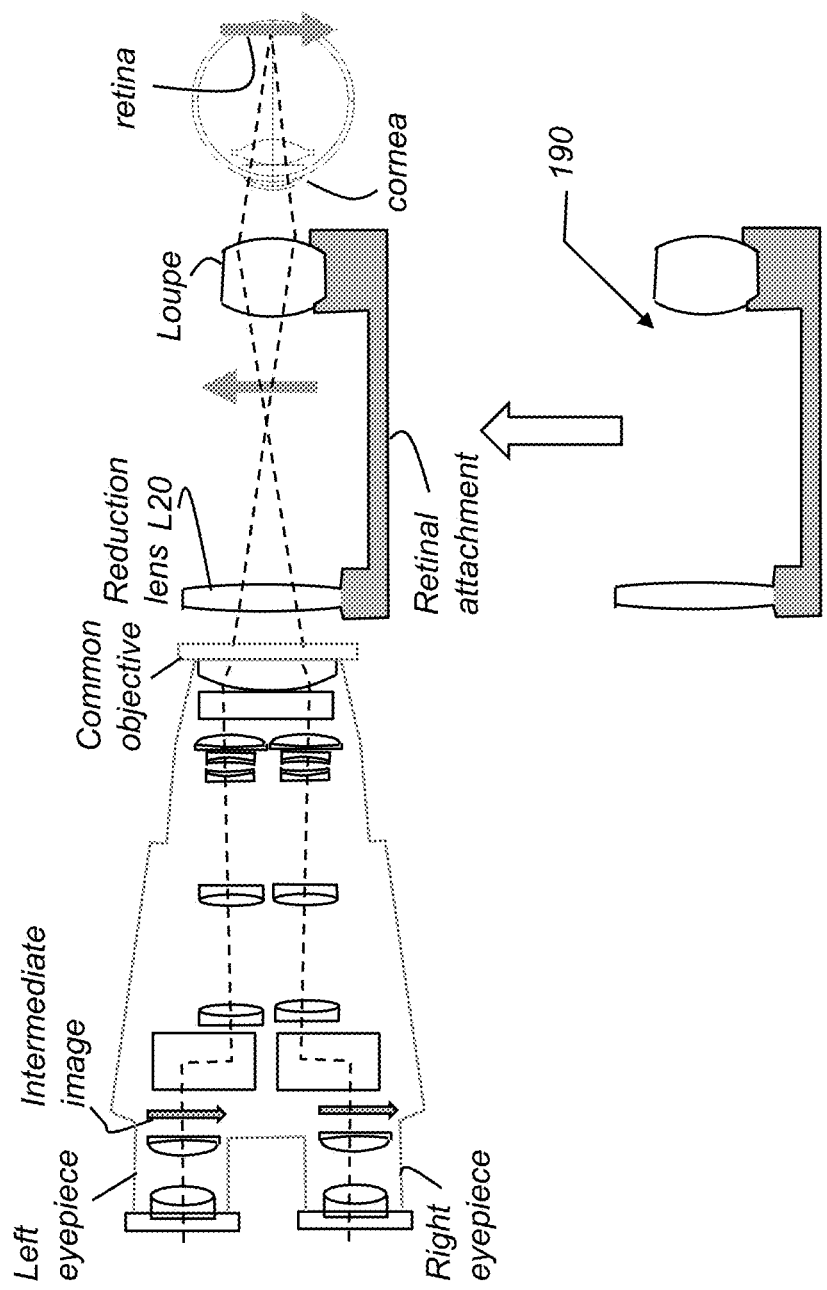
FIG. 1B shows a conventional method for viewing the retina wherein an insert having two lenses is disposed between the objective of FIG. 1A and the cornea.

FIG. 1B shows a conventional method for viewing the retina wherein an insert 190 having two lenses is disposed between the objective of FIG. 1A and the cornea. A reduction lens L20 is placed close to the objective; the smaller loupe or surgical lens is placed near the patient's eye. The surgeon can either look at the retina with the insert in position or at the cornea with the insert removed. In both cases, imaging is commonly done in 3D.

Figure 2:
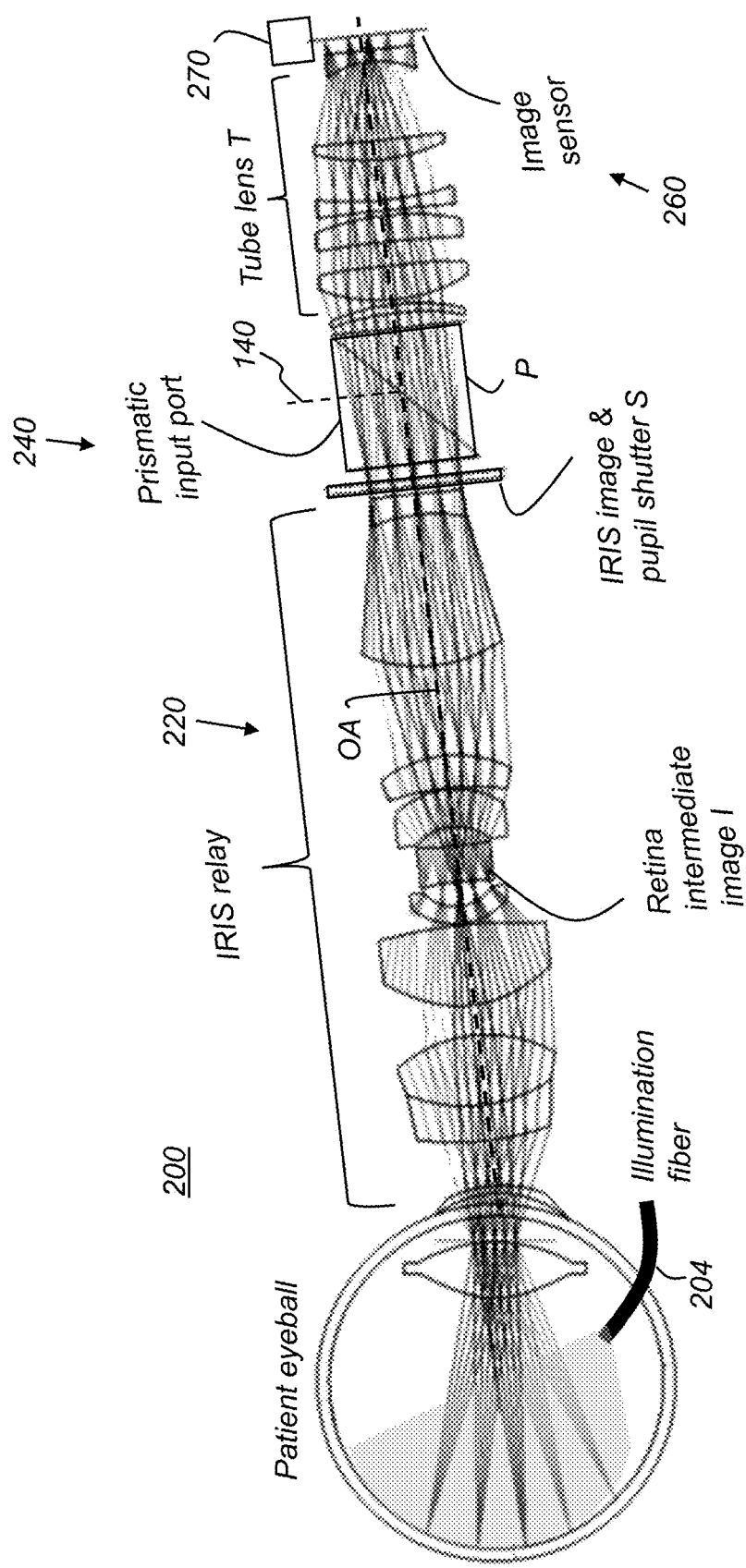
FIG. 2 is a schematic diagram showing a 3D stereomicroscope apparatus embodiment according to the present disclosure.

When alternating between the imaging modes shown in FIGS. 1 and 2, the image that appears is inverted. To remedy the confusion, an optical image inverter (not shown) can be added for rectifying the image display.

FIG. 2 is a schematic that shows an embodiment of a retina imaging attachment 200 according to the present disclosure. The retina is imaged by a retina-dedicated compact system. There are no eyepieces to limit the positioning of this system so it can point at different angles into the eye as shown, for example, for a viewing angle of 6 degrees off the optical axis of the patient's eye.

The system has three basic subsystems:
1. Iris relay 220. The iris relay 220 relays the inaccessible patient's iris, which is positioned inside the eyeball, about 3 mm behind the cornea, to the shutter plane shown. The relay is an afocal relay which accepts essentially collimated beams from the eyeball and relays this light into collimated beams directed toward at the shutter plane.
2. Shutter S and input port subsystem 240. The shutter element S is placed at the image plane of the iris. When fully open, imaging of the retina is done with the full iris and with a large numerical aperture, providing the highest resolution available from the optical system. Shutter S can be a MEMS or electronic device which can be a digitally controlled array allowing variable opacity, for example, to provide a variety of shapes of transparent openings. Alternately, shutter element S could be a digital micromirror device (DMD), similar to the DMD elements made by Texas Instruments as part of a Digital Light Processor (DLP) system, or similar device. According to an embodiment of the present disclosure, shutter element S could be provided using a liquid crystal device (LCD) array. To image the retina in 3D, the aperture dimensions, spacing, and relative angular placement can be modified as explained subsequently. The prismatic input port, with a combiner prism P, allows for added functionality such as potentially incorporating optical coherence tomography apparatus (OCT) capabilities, as described in more detail subsequently, along with other features enabled in this embodiment.
3. Digital camera or other image sensor 260. The digital camera can consist of the sensor and the corresponding lens, which is also called the tube lens. The tube lens T shown in FIG. 2 for this camera has an externally accessible entrance pupil which is placed at the shutter plane. An optional actuator 270 can also be provided for controlling image sensor 260 movement for light field imaging, as described subsequently.

There is also an intermediate image I of the retina within the relay.

The retina is commonly illuminated in surgery through openings in the eyeball through which illumination fibers 204 are inserted as shown in FIG. 2.

The IRIS relay 220 can have any suitable magnification. The relay shown in the example of FIG. 2 has 2× magnification, so that the iris image at the shutter element has a diameter of 6 mm when the actual iris diameter is 3 mm. The beam angles into the shutter S are half of the system FOV, so that for a 50-degree FOV as shown, the light at these angles extends a full 25 degrees at the shutter.

The sensor can be contained within a retinal imaging apparatus that is detachable from a larger stereomicroscope system and remains in signal communication with the system. Alternately, sensor 260 can be an integral part of the stereomicroscope that is provided at the imaging plane.

At the input port, light along a primary optical path that extends from the patient's eye to image sensor 260, such as along an optical axis OA in FIG. 2, can be combined with light along a secondary optical path 140, shown orthogonal to optical axis OA at input port 240. The secondary optical path can convey some portion of the image-bearing light to another optical sensor or system. Alternately, the second optical path can convey a light signal, such as an OCT sample signal or other signal that can be at a wavelength outside the visible spectrum. The light signal on the secondary optical path can be in the near ultraviolet (UV) range below 380 nm, or in the infrared (IR) range above 750 nm, for example.

Figure 3:
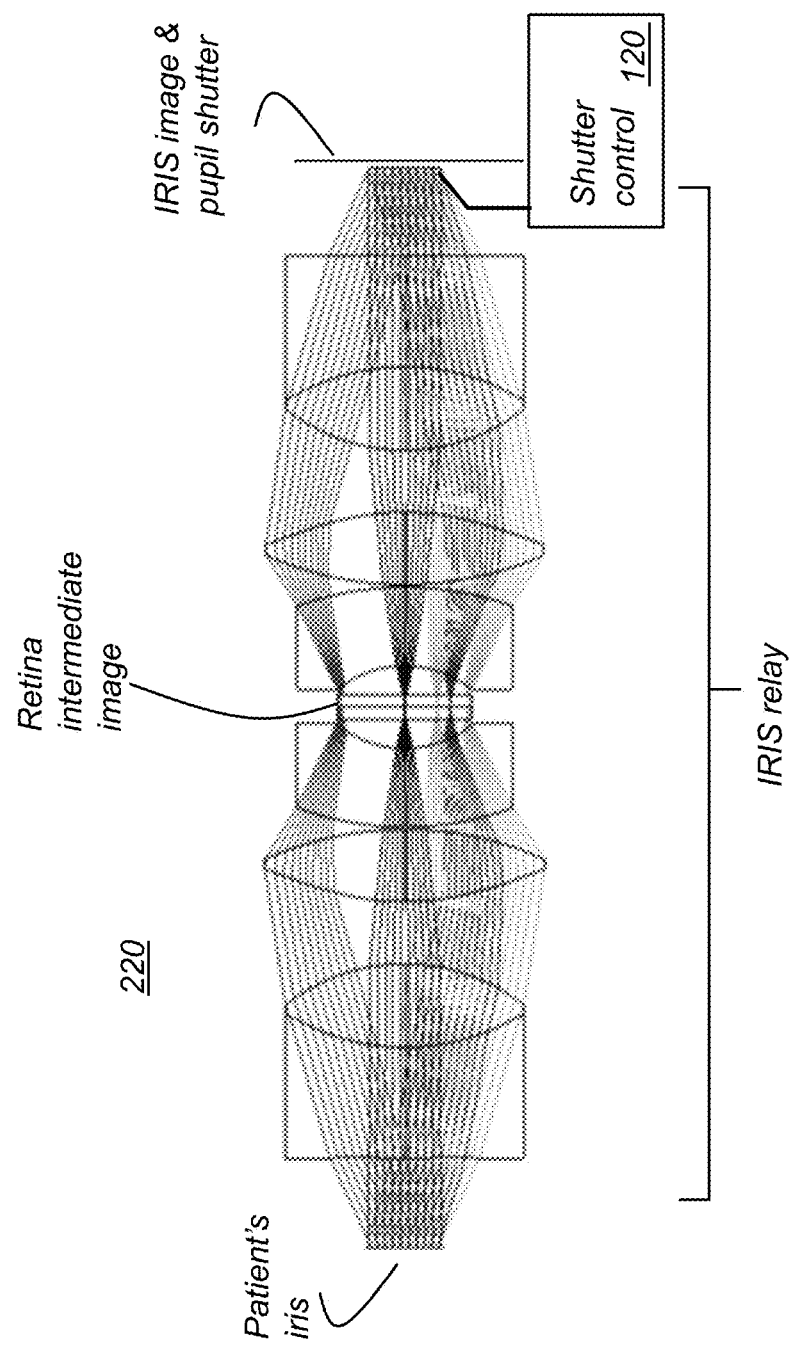
FIG. 3 is a 1:1 iris relay according to an embodiment of the present disclosure.

FIG. 3 shows an exemplary relay with 1× magnification. A 1:1 afocal iris relay has the advantage of having the shortest total distance from the iris to the shutter. This arrangement is also simpler since it is symmetrical, with half the number of different elements in this relay compared to the relay shown in FIG. 2. A shutter control processor 120 provides the logic and control elements needed for determining shutter shape and sequencing, as described in more detail subsequently.

Symmetry about the optical axis also makes the relay simpler due to inherent properties of symmetrical systems, which do not suffer from aberration, and which are linear with the field such as lateral color, coma, and distortion.

However, due to the larger angles at the shutter S, the working distance at the shutter space is shorter and the design of the input prism (not shown in FIG. 3 but shown in FIG. 2) is more challenging.

Sterilization

In the conventional system as shown in FIGS. 1A and 1, the distance between the patient's eye and the stereomicroscope is unchanged. Due to the proximity of the loupe to the patient, its sterility must be maintained. In the event of loupe contact with the patient, the procedure stops. At this point, a sterilization cycle must be executed for the loupe and, in some cases, for the mechanical support and even the reduction lens. This inadvertent contact can involve numerous steps for removal and sterilization.

Figure 4:
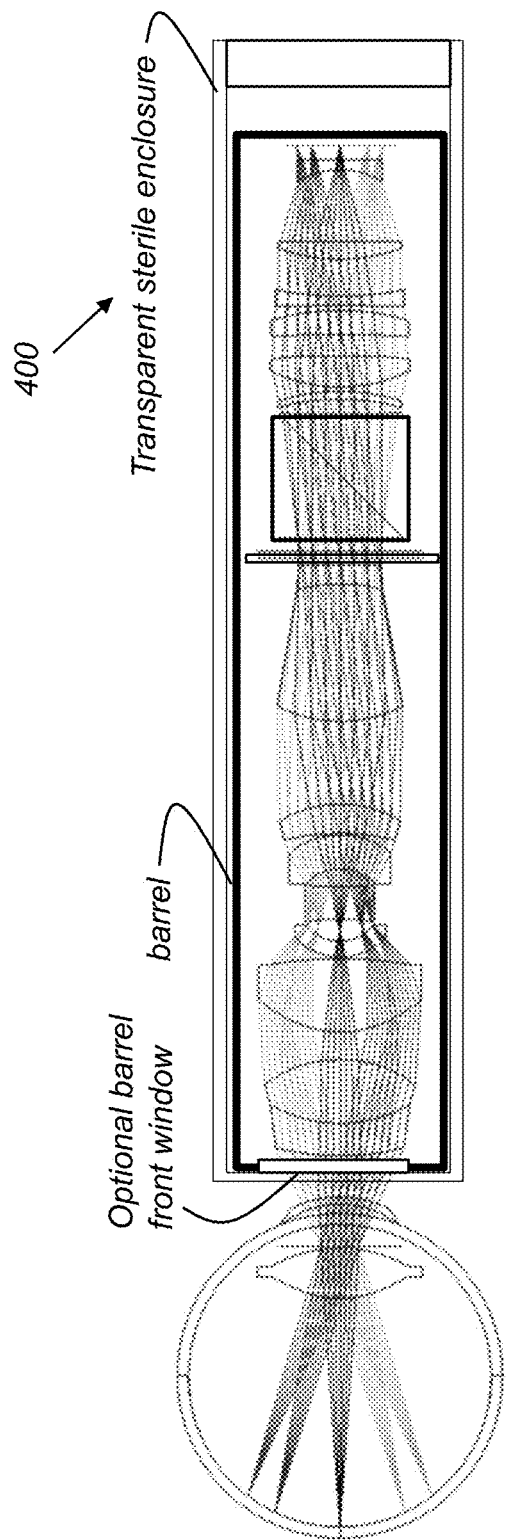
FIG. 4 shows the retina imaging attachment provided within a sterilized enclosure.

As shown in FIG. 4, embodiments of the present disclosure provide enclosure of the optics system within a cylindrical housing 400. This enclosure can be made of a transparent polycarbonate. When sterilization is required, the enclosure can be replaced. The enclosure can be a disposable element, or it could be replaced with a previously autoclaved unit, for example.

Autostereoscopic Imaging:

3D imaging can be achieved by forming two sub-apertures, placed essentially at the image of the patient iris, and obtaining the retina images from these two sub apertures, having a convergence angle between them.

In conventional apparatus, the two sub-apertures are formed at the large objective of the microscope. Commonly, the objective has a diameter of 3 inches, in which two sub apertures each of about 1.25-inch diameter are placed side by side. When viewing the retina, these two apertures are imaged to the iris by the reduction lens and the loupe shown in FIG. 1B. Thus, typically, within the 3 mm iris diameter, two sub-apertures are formed, side by side, each sub-aperture of about 1.25 mm diameter. In conventional apparatus, the images obtained from these two sub-apertures can be conveyed to the surgeon's eyes respectively and/or can be conveyed to two cameras or other image sensors.

Because the limiting diffraction spot size is dependent on aperture dimensions, the resolution of each of the images obtained by the small sub-apertures is significantly lower than the resolution available through the full iris aperture. Thus, the resulting stereographic images are reduced in resolution when compared with monoscopic images that can be formed using the same optical system.

As conventional 3D microscopes have been constructed, the viewing surgeon cannot switch imaging modes at will, changing from 3D presentation to higher resolution monoscopic imaging. In an embodiment of the present disclosure, the Applicant remedies this shortcoming of existing 3D microscopes, allowing the viewing practitioner to switch readily between monoscopic and stereoscopic or 3D image presentation using a shutter element.

Figure 5A:
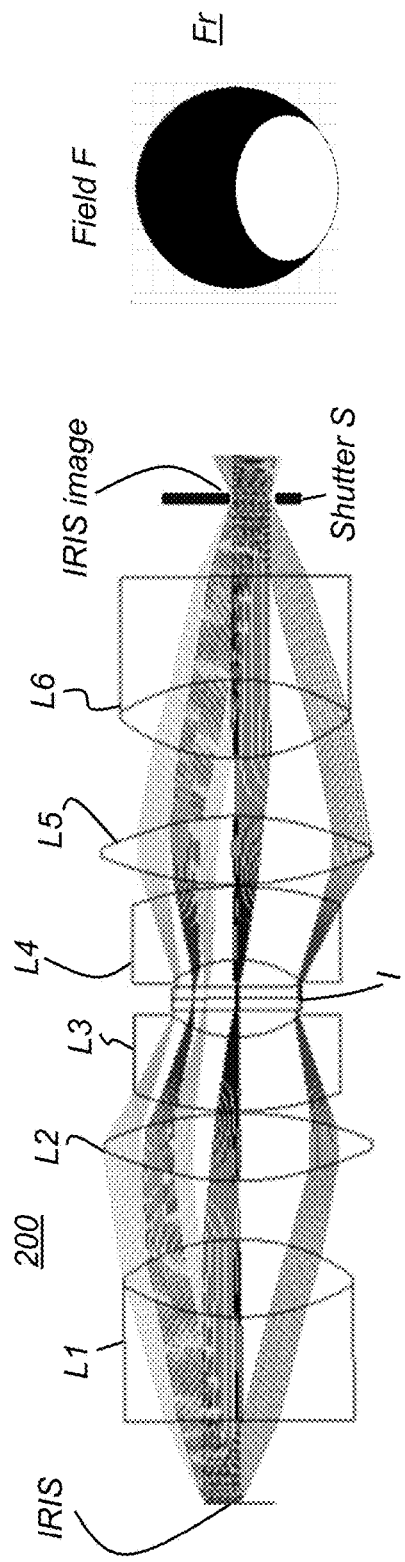
FIGS. 5A-5C are schematic diagrams that show the 3D sequential operating modes available when using the shutter.
Figure 5B:
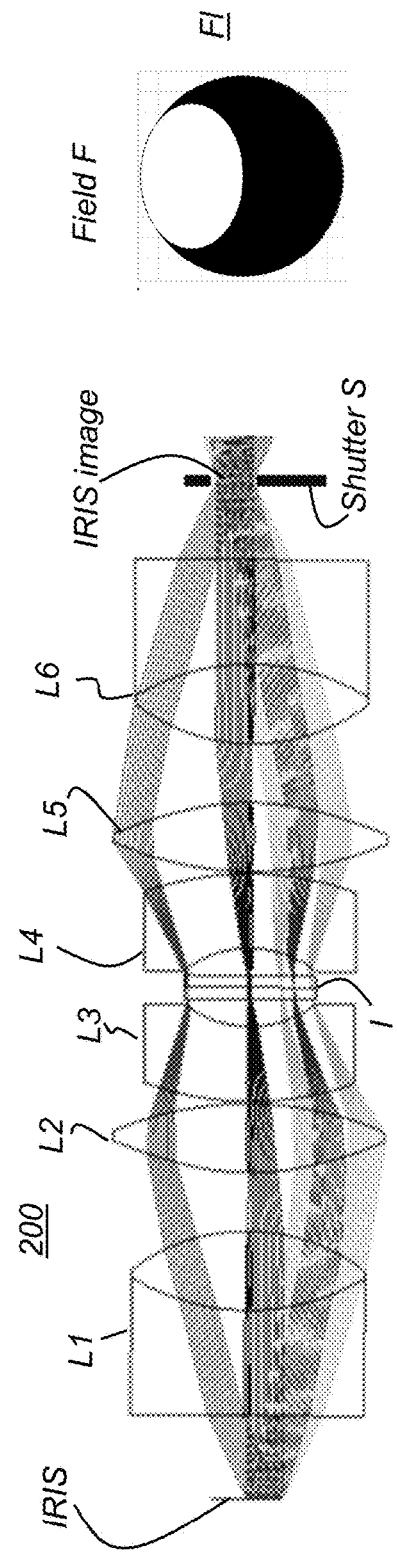
Figure 5C:
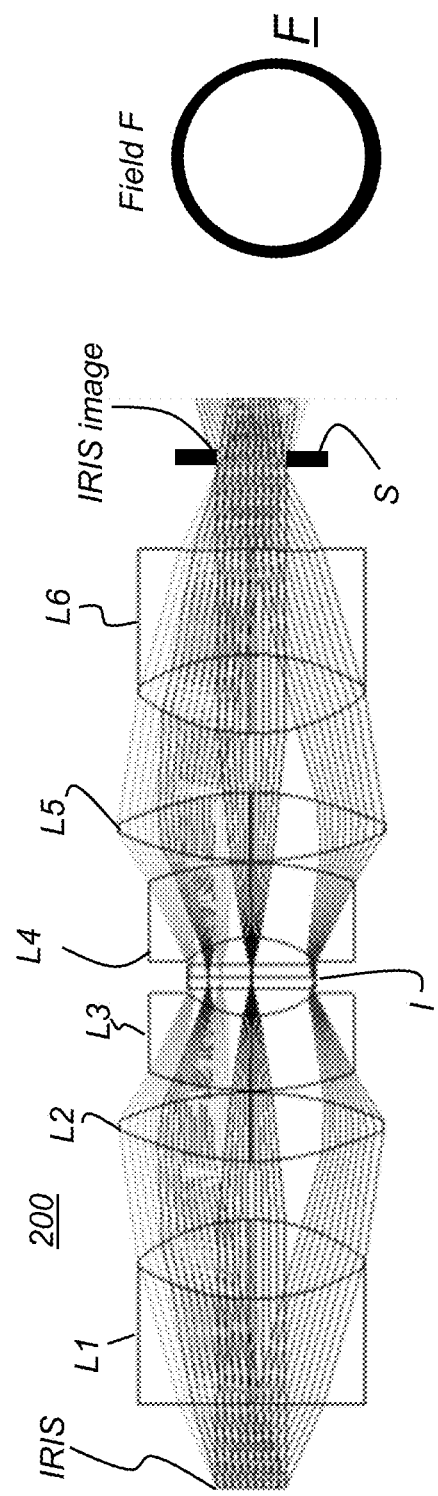

FIGS. 5A-5C show how a shutter S can be used to provide the benefit of alternating between high resolution monoscopic imaging and stereo 3D imaging.

Using the symmetrical relay of FIG. 3, the iris image allows two smaller apertures for the two 3D channels, shown in the image field F in FIGS. 5A-5C. The image field F has a portion Fl suitable for the left eye, as shown in FIG. 5B and, correspondingly, a portion Fr for the right eye, as represented in FIG. 5A.

By controlling the timing sequence for shutter S apertures, images can be obtained sequentially for the right and left eye, wherein each image is viewed through the corresponding sub-aperture at the iris while covering the same full field of the retina. To avoid flicker effects and provide continuous image content, a sequential switching cycle for shutter operation can be performed. Cycling of shutter S switching for sequential presentation, alternating the view of left-eye and right-eye image field portions Fl and Fr, should be at a sufficient rate, such as at frame rates higher than 50 Hz, for example.

This method of obtaining stereopsis or binocular vision in FIG. 19 using shutters has been used in some projection systems and also in in-home TV entertainment systems, wherein the display or projection screen rapidly alternates between rendering left- and right-eye image content, in synchronization with shutter glasses worn by the viewer. A number of major companies provide such systems, such as SSG2100AB Active Shutter 3D glasses from Samsung Electronics, for example. Embodiments of the present disclosure can use rapid alternation of displayed content for improved visibility of patient anatomy by stereopsis, which can be implemented on demand by the viewing surgeon or other practitioner.

The viewing surgeon can also open up the full shutter element for monoscopic viewing, as shown schematically in FIG. 5C. Shutter S control can be provided using any of a number of types of manual switches or selection devices that are in signal communication with shutter control processor 120 (FIG. 3). Shutter control 120, in turn, energizes the electronic array or other device that controls shutter aperture dimensions, spacing, and relative positioning; for example, shutter control 120 can vary the azimuth angle between left- and right-eye apertures.

According to an embodiment of the present disclosure, audible command entry to a microphone (not shown) that is in signal communication with shutter control processor 120 can be used for hands-free switching between 3D and monoscopic display. Feedback from sensors that detect eye position of the viewer can alternately be used for providing input signals to shutter control processor 120. Gaze detection techniques and processing are familiar to those skilled in the optical arts and can be applied for use with wearable display apparatus, such as head-mounted displays (HMDs), or can be used with other displays including display screens, for example.

Using the full aperture as in FIG. 5C allows the optical system to provide high resolution. In addition, the full aperture provides better signal to noise ratio (SNR) at the sensor than is available using dual aperture configurations.

Light levels allowed at the retina are limited due to phototoxicity. The brightness at the sensor, in NITs (or $Cd/m^2$), for a perfect system with negligible transmission loss, is the same as the brightness at the retina.

The power in lumens or Watts collected by the iris is proportional to the iris area. Thus, for the optics system of the present disclosure, the best achievable SNR is obtained using a large monoscopic field of FIG. 5C. The apertures can also be sequentially switched to the different configurations shown in FIGS. 5A, 5B, and 5C, thus providing the surgeon the possibility a combined image which has high resolution and high SNR.

Figure 6A:
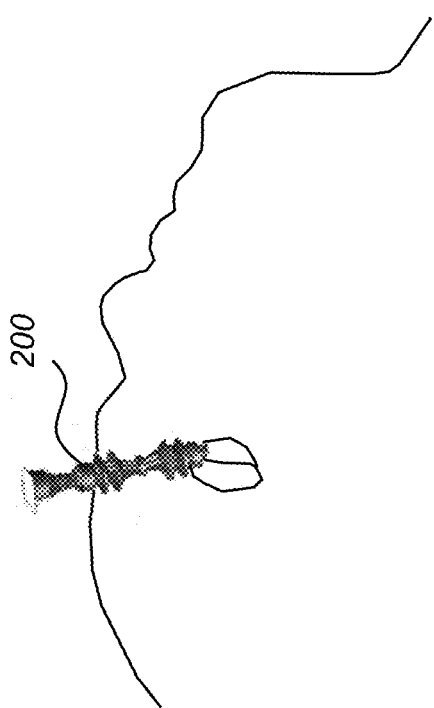
FIGS. 6A and 6B are perspective views showing use of the retina imaging attachment.
Figure 6B:
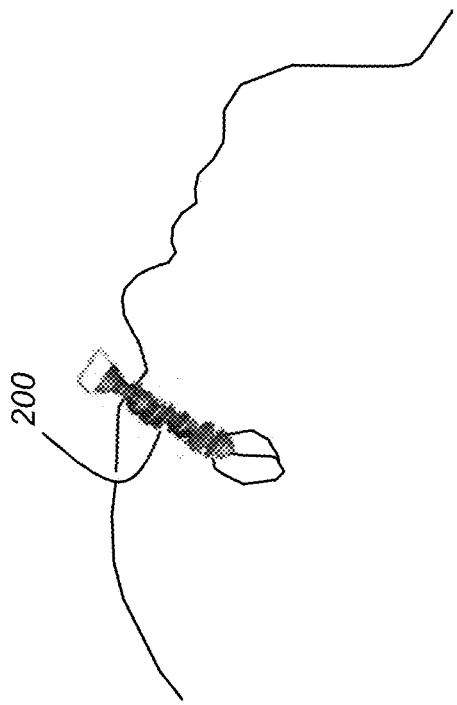

FIGS. 6A and 6B show retina microscope attachment 200 as used in surgery, aimed into the patient's eye at different angles in order to cover different retina regions. Preferably an articulated arm (not shown) can be used for controlled orientation and aiming of attachment 200.

The capability to shift the shutter S arrangement between partial aperture (FIG. 5A or 5B) and full aperture (FIG. 5C) settings allows the surgeon to have either high resolution or increased depth of field. Resolution variation is linear with F/#; depth of field variation is quadratic with F/#.

Figure 7A:
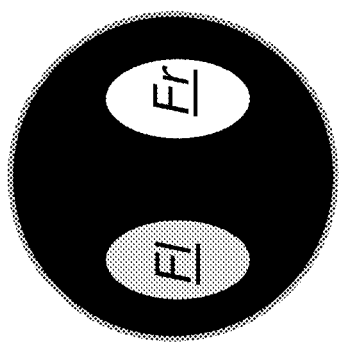
FIGS. 7A-7D are schematic diagrams that show aperture shutter modes for increased depth of field.
Figure 7B:
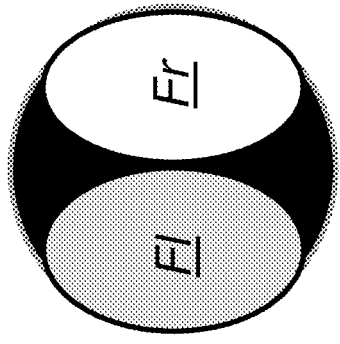

By way of example, FIGS. 7A and 7B show two 3D configurations at the shutter S. FIG. 7A is the default arrangement for 3D viewing. FIG. 7B shows a configuration that allows essentially the same stereopsis as in FIG. 7A, but with larger depth of field. This larger depth of field comes at the cost of reduced resolution and lower SNR.

According to an embodiment of the present disclosure, system operation can be sequentially switched between the two modes of FIGS. 7A and 7B. With alternating images provided at a suitable frame rate, a composite can be formed. To viewer perception, such a composite provides both high resolution and large depth of field. Demonstration of this composite function was attempted as "FusionOptics™" by Leica Microsystems, Mannheim, Del. (Model M691 Surgical Microscope).

In contrast with conventional circular apertures, sub-apertures used for 3D viewing can be highly elliptical in shape, as shown in FIG. 7A. The elliptical aperture can have almost twice the area of the conventional circular aperture, thus providing a larger collection area and improved SNR over circular aperture geometry.

Figure 7C:
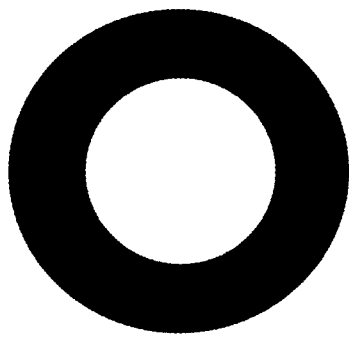
Figure 7D:
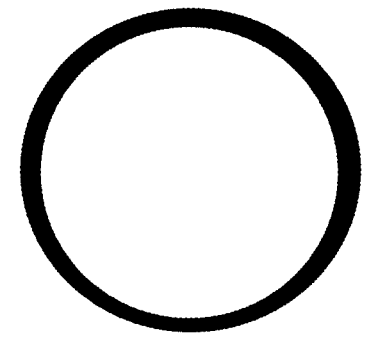

The same tradeoff between depth of field and resolution can also apply in monoscopic viewing mode, as shown in FIGS. 7C and 7D. Sequential switching of shutter S can also be used for monoscopic imaging.

Figure 8A:
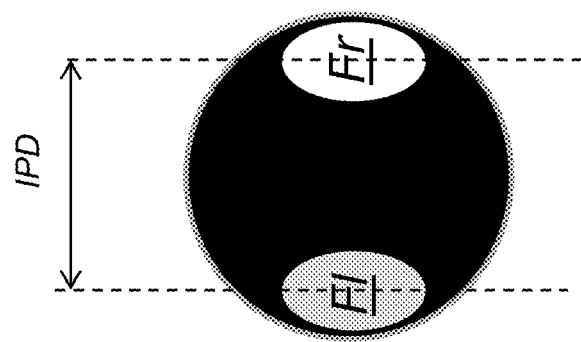
FIGS. 8A and 8B are schematic diagrams that show an aperture mode with adjustable stereopsis.
Figure 8B:
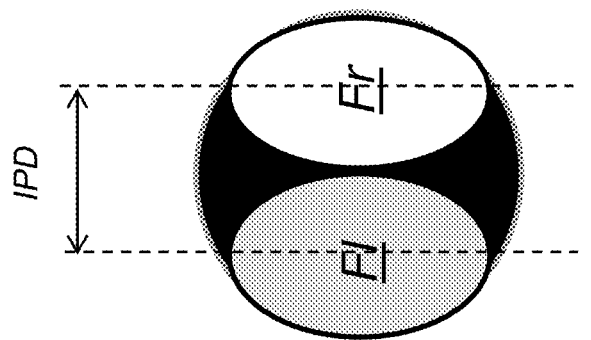

FIGS. 8A and 8B show an aperture mode that allows adjustable stereopsis, employing shutter S to adapt stereopsis to the viewer's inter-pupil distance (IPD) by modifying the shape and relative location of the left- and right-eye field portions Fl and Fr, respectively. This solution can improve 3D perception and depth of field at the cost of some loss of resolution and decrease in signal-to-noise ratio (SNR).

Figure 9B:
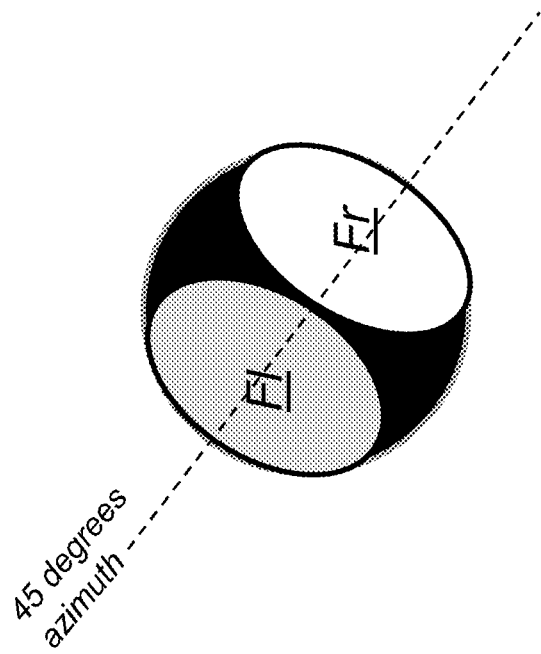
FIGS. 9A and 9B are schematic diagrams that show an aperture mode with an adjustable IPD azimuth.
Figure 9A:
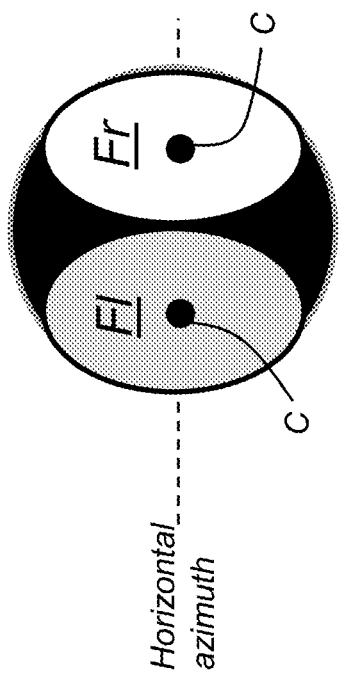

Another feature of the apparatus of the present disclosure relates to the capability to change the IPD azimuth, as shown schematically in FIGS. 9A and 9B, defined from a center C of Fl to center C of Fr, for example. The azimuth angle can be adjusted to any suitable angle from 0 to 90 degrees, according to a signal from shutter control 120 (FIG. 3). By way of example, FIGS. 9A and 9B show the default 0-degree horizontal azimuth and an adjusted azimuth angle of 45 degrees, respectively. This capability for changing the relative angle between left and right field portions Fl and Fr enables improved 3D perception of various structures. This can include, for example, visibility of inclined narrow structures such as a horizontal edge of a thin film, tissue, or other planar object that could be otherwise difficult to perceive without this angular change.

Figure 10B:
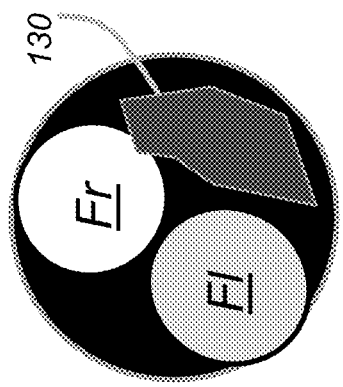
FIGS. 10A and 10B show an aperture mode adjusted to avoid cornea defects.
Figure 10A:
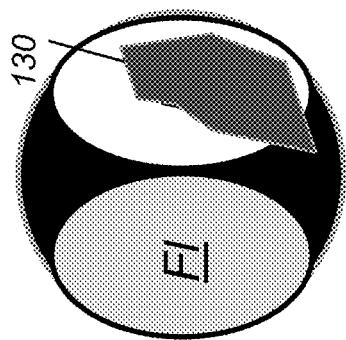

Another feature of the optical apparatus of the present disclosure relates to the capability to adjust the Fl and Fr sub-apertures at the iris to be able to provide stereopsis and to be able to view around or similarly avoid cornea defects or cataracts as shown in FIGS. 10A and 10B.

In FIG. 10A, a cataract or other defect 130 obstructs visibility for right-eye field portion Fr. Adjustment of the relative position of portions Fl and Fr, with a change of azimuth angle, allows the viewer to work around the obstacle presented by cataract or other defect 130 in order to view portions of the retina that would otherwise be obstructed.

The use of a variable shutter element that is capable of alternating between stereoscopic image presentation and monoscopic image presentation can be extended to other types of optical systems and can be an effective tool for improving visualization in medical imaging and other imaging fields. This approach provides the viewer with a trade-off between resolution and 3D imaging that can have particular benefits for surgery.

An alternate method for extending the depth of field uses Extended Depth of Field (EDOF) filters. These filters, as described, for example, by Cathey et al. in US Patent Application Publication No. 2008/0174869 A1 entitled "Extended Dept of Field Optical Systems", can be placed symmetrically, one for each left- and right-eye portion Fl and Fr. Exemplary filters used for extending depth of field can be, for example, phase plates having significant aberration, such as elliptical coma, wherein the image is degraded in a known manner, to be retrieved by processing over a larger depth of field.

The device of the present disclosure also allows the use of volumetric imaging, such as employing techniques currently termed temporal light-field imaging. This feature allows for the sensor 260 to be moved along its z axis, preferably in the monoscopic imaging mode, thus exploring the retina by capturing image content at two or more different depth locations. An optional actuator 270, as shown in FIG. 2, can be coupled to sensor 260 and energized for use in controlling sensor 260 movement. The volumetric information thus retrieved can be rendered into stereoscopic information and presented to the viewing surgeon as 3D stereoscopic retina images. Alternately, instead of moving the sensor over a number of z-axis positions, a variable phase element (not shown) can be disposed at the image of the iris to accomplish variable focusing.

Figure 11:
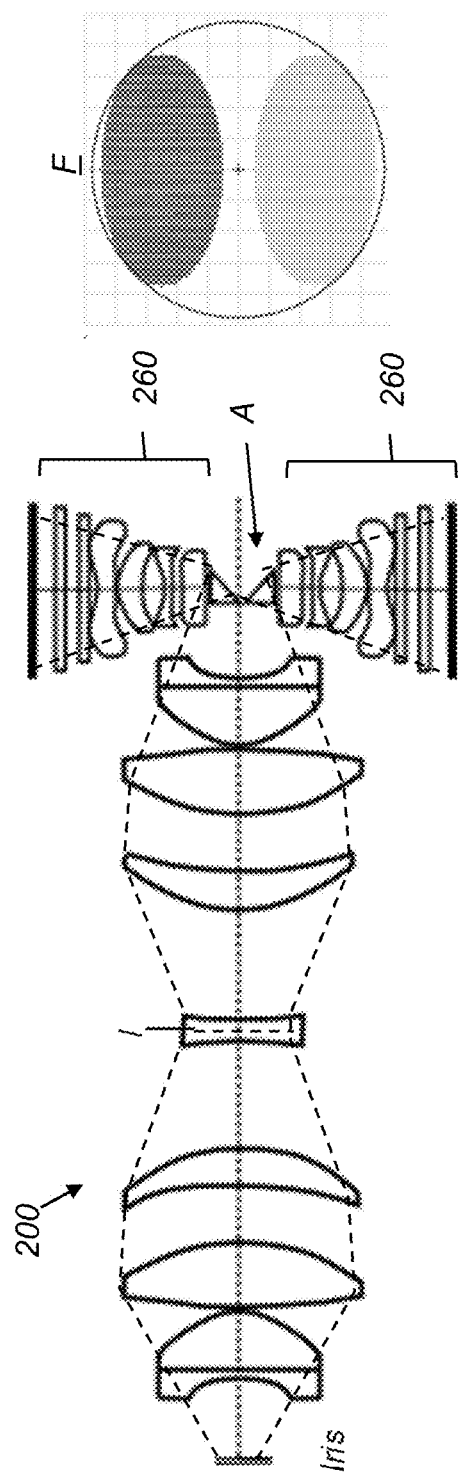
FIG. 11 shows the use of two cameras in an alternate embodiment.

In another embodiment of the current disclosure, the 3D information is retrieved by following iris relay 200 with a pupil splitter and left- and right-eye view cameras as sensors 260, as shown in FIG. 11. This arrangement provides two stereoscopic imaging channels in a manner that can be more compact and maneuverable than the conventional arrangement shown in FIGS. 1A and 1B.

Exemplary OCT Input

Figure 12:
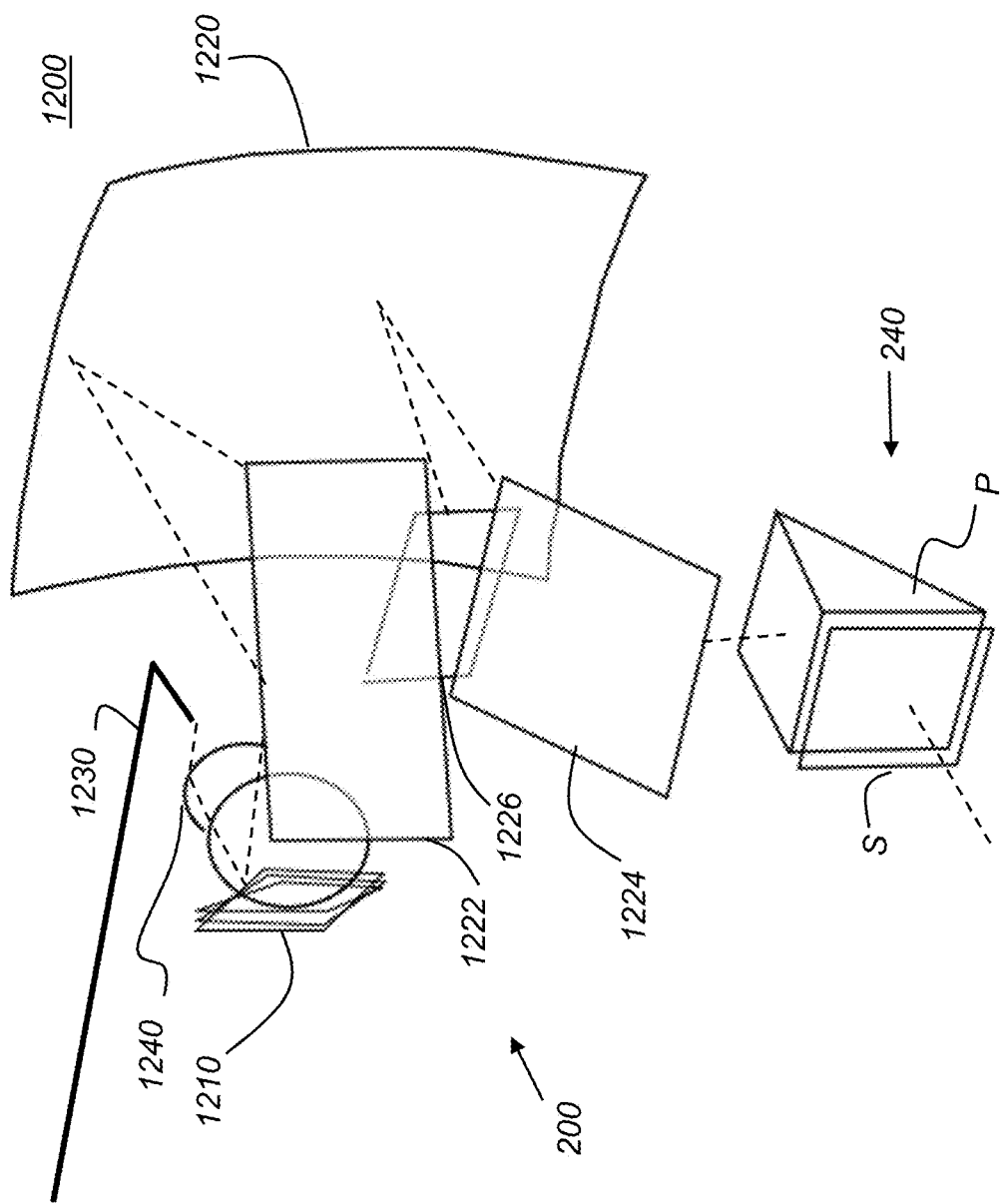
FIG. 12 is a perspective view of a relay apparatus having a scanner that has two MEMS (Micro-Electromechanical Systems) mirrors that cooperate to provide reflection similar to a 2-D gimballed mirror.
Figure 13:
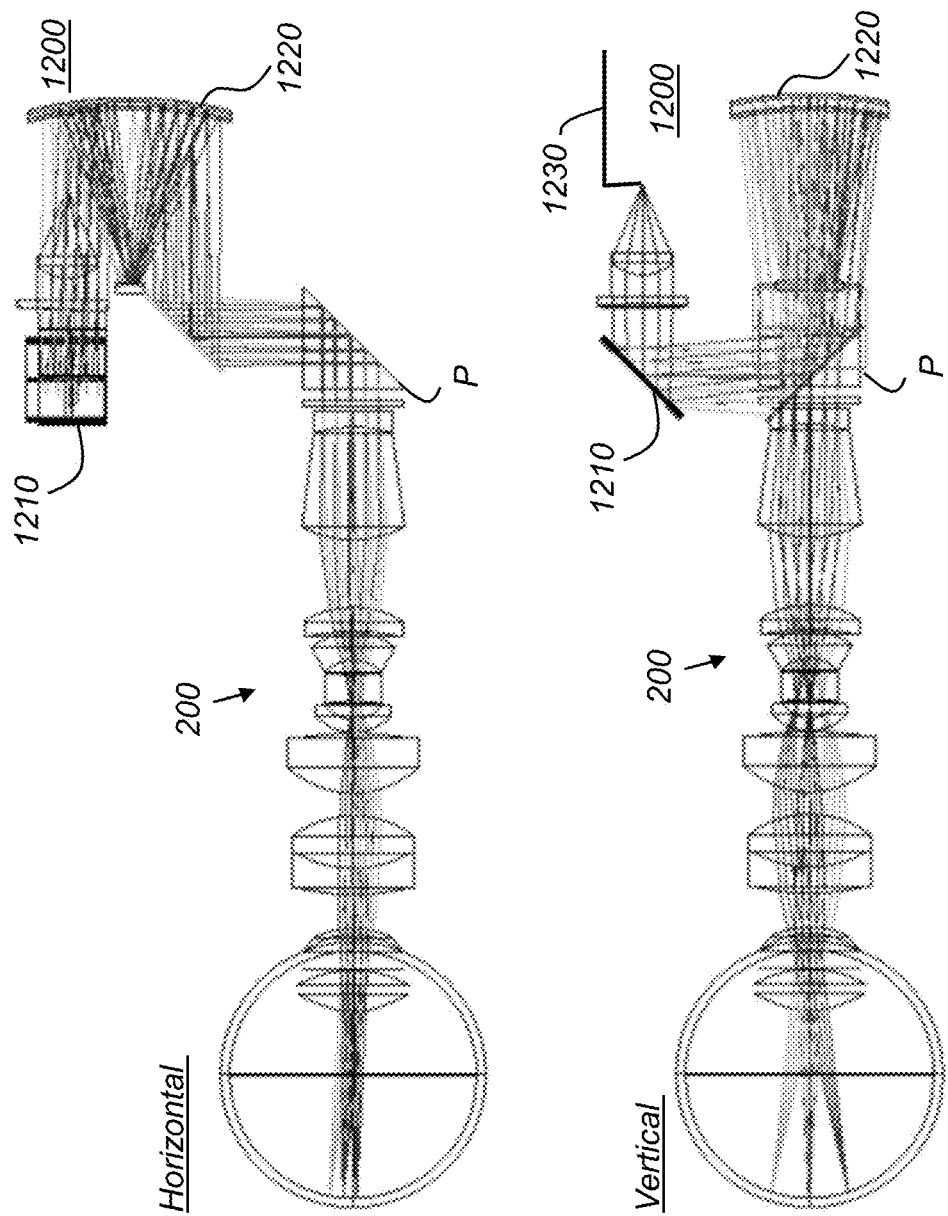
FIG. 13 shows two schematic vertical and horizontal views of the scan path to the combining prism for OCT sample light.
Figure 14:
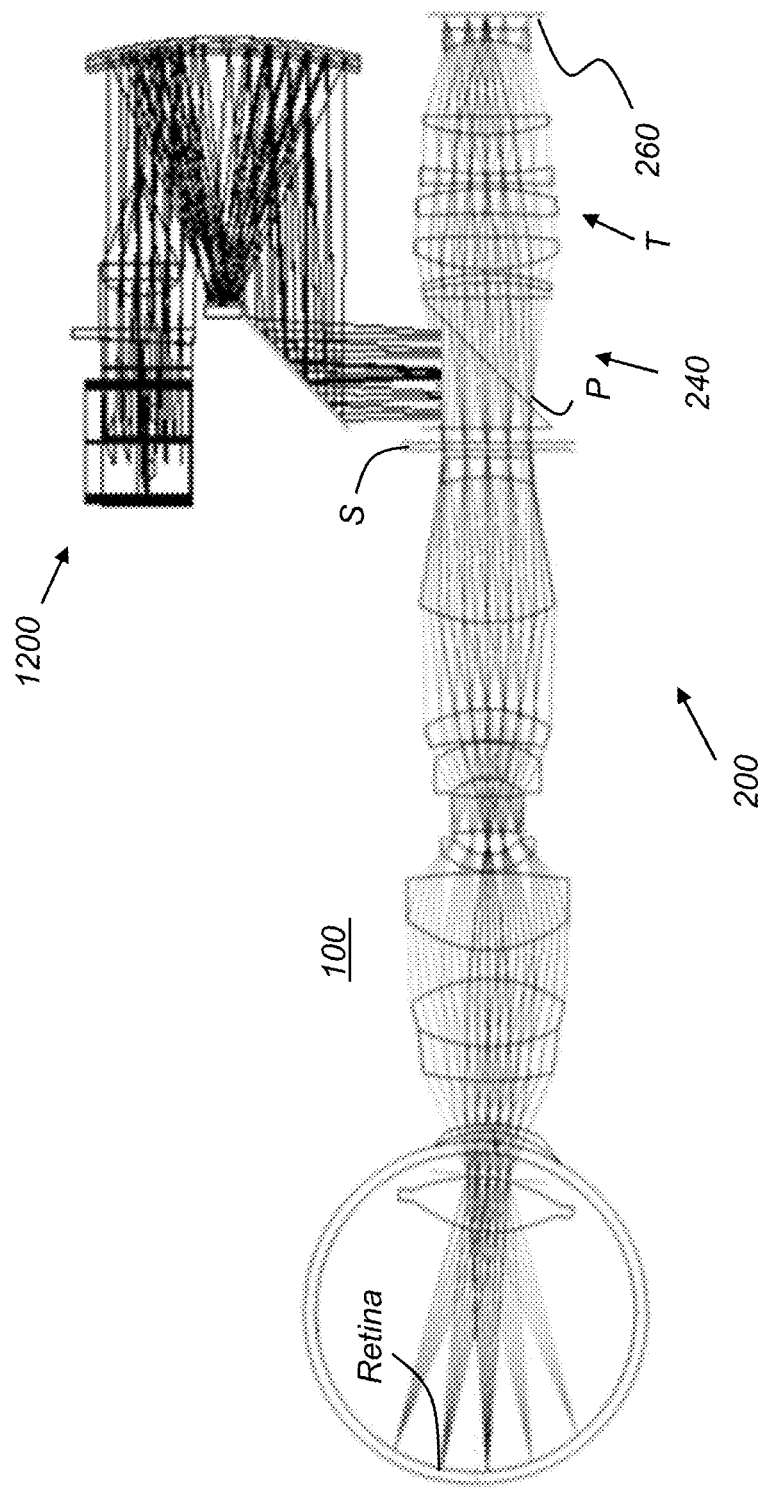
FIG. 14 is a schematic side view that shows stereomicroscope optics with a relay combining OCT with the shuttered light path.

Shutter and input port subsystem 240 can be used to support a number of auxiliary options, providing access to the optical axis of the microscope apparatus. FIGS. 12, 13, and 14 show how an OCT apparatus can be incorporated with microscope optics of attachment 200 according to an embodiment. An afocal relay 1200, such as an arrangement of curved mirrors as described in U.S. Pat. No. 8,274,720 entitled "Concentric afocal beam relay" to Kessler, incorporated by reference herein, can be used to provide a diffraction-limited relay for support of OCT scanning. FIG. 12 is a perspective view a of relay apparatus 1200 having a scanner 1210 that has two MEMS (Micro-Electromechanical Systems) mirrors that cooperate to provide reflection similar to a 2-D gimballed mirror. An OCT sample fiber 1230 directs the OCT sample beam to and from a collimator 1240 and to scanner 1210. The light from scanner 1210 is directed to a primary concave mirror 1220 and to secondary convex mirror 1226, and back to primary mirror 1220, with additional folding of the light path to and from primary mirror 1220 provided by mirrors 1222 and 1224. The OCT beam to and from the eye is then combined along the optical path to the eye with the image-bearing light by shutter S and prism P of shutter and input port subsystem 240. The received signal from the scanned sample follows the same light path as the signal sent to the sampled retina.

According to an embodiment of the present disclosure, scanner 1210 can scan 12×6 mechanical angles at 6 mm diameter, 24×12 degree full-scan angles converted at the iris to 25×12 degrees. Along one axis, the OCT scan can cover the full retinal field of view (FOV) of the microscope with this arrangement.

The schematic views of FIG. 13 show vertical and horizontal views of the scan path for OCT sample light to and from the eye through combining prism P. The vertical direction in this example allows scanning at 25 degrees; the horizontal at about 12.5 degrees. FIG. 14 shows the overall stereomicroscope 100 optics with relay 1200 combining OCT with the shuttered light path for retinal imaging.

Impact on Resolution

Figure 15A:
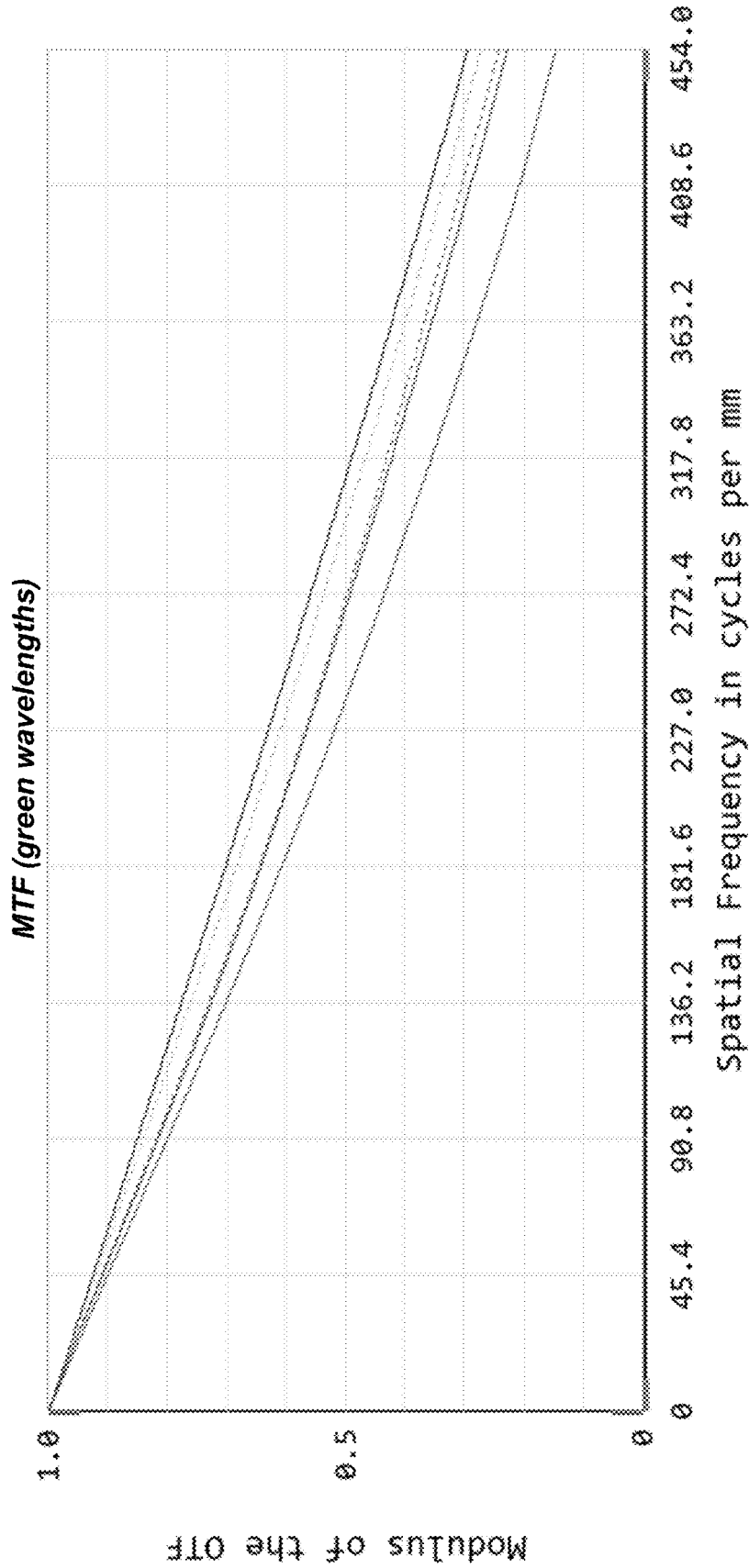
FIGS. 15A and 15B are Modulation Transfer Function (MTF) graphs for monoscopic and stereoscopic viewing, respectively.
Figure 15B:
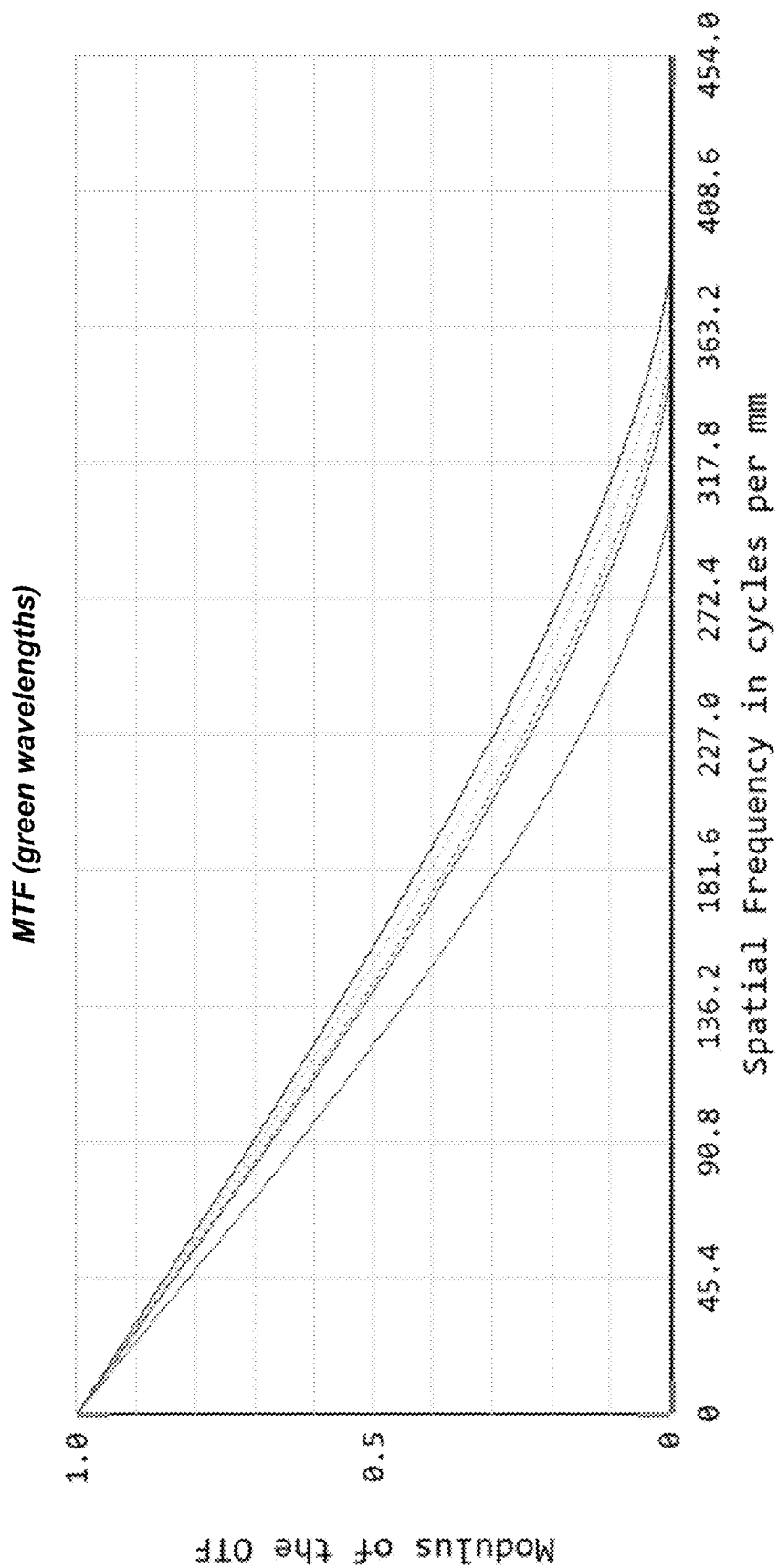

One advantage of the optical apparatus described herein relates to the capability to switch between monoscopic and stereoscopic views of the subject patient's retina, as was described previously with reference to FIGS. 7A-7D. One tradeoff between the two imaging modes relates to image resolution, as can be best shown using Modulation Transfer Function graphs, as given in FIGS. 15A and 15B. The values obtained are for green wavelengths. FIG. 15A shows the higher resolution capability provided using the single aperture monoscopic mode. FIG. 15B shows the decreased resolution that is available using the dual-aperture stereoscopic mode.

External Retinal Illumination

Figure 16:
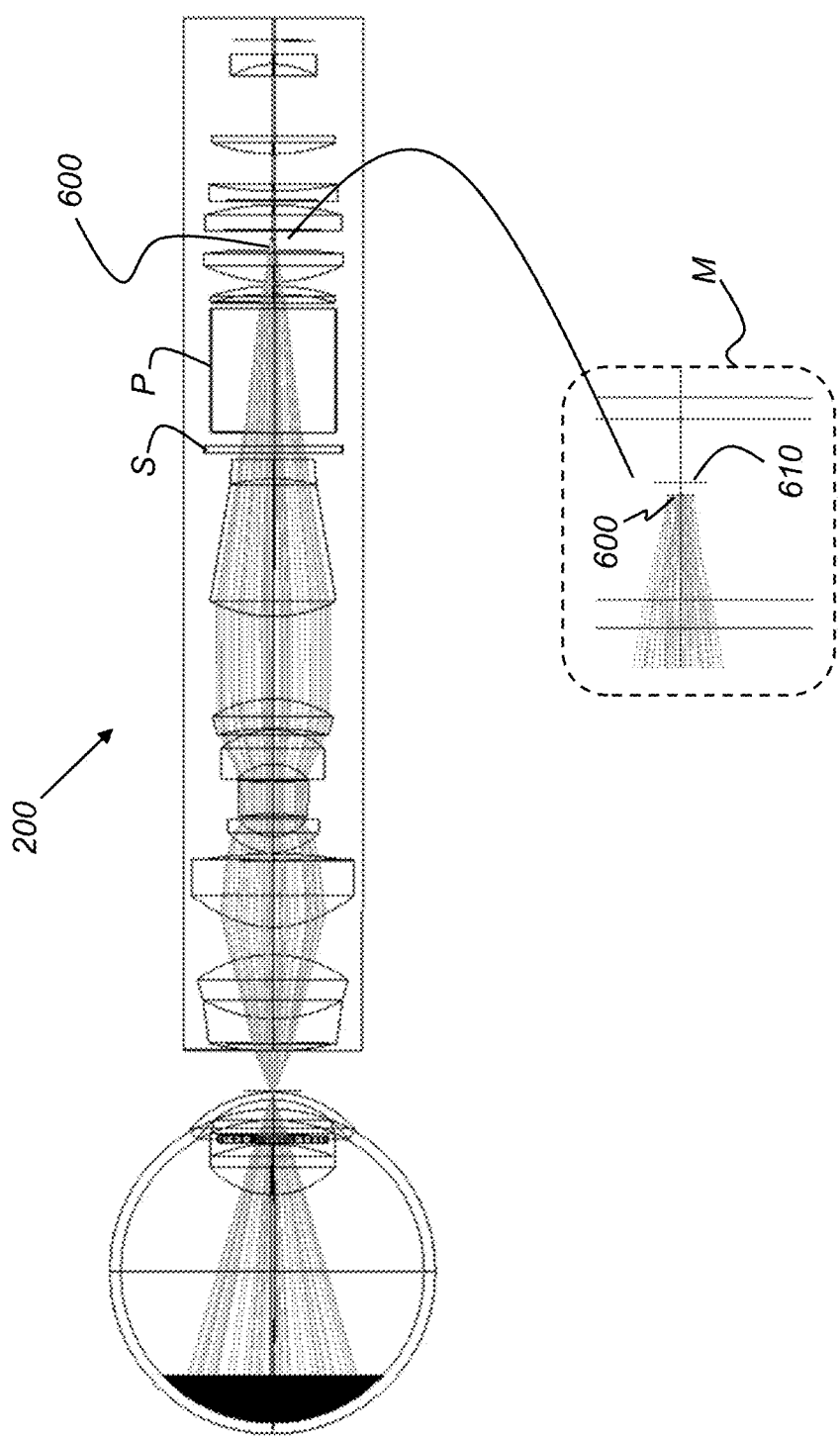
FIG. 16 is a side view schematic that shows an optional illumination arrangement for the optical attachment using optical fiber.

The side view schematic of FIG. 16 shows use of an optional on-axis fiber source 600 disposed behind the prism P for providing retinal illumination on-axis. The source 600 is positioned behind the shutter S, optically conjugate to the cornea. A blocker 610 is provided behind the source 600 to remove cornea glare from the reflected signal, as showed in magnified portion M. Illumination could alternately provide the equivalent of conventional slit lamp illumination.

Adaptive Optics (AO)

Figure 17:
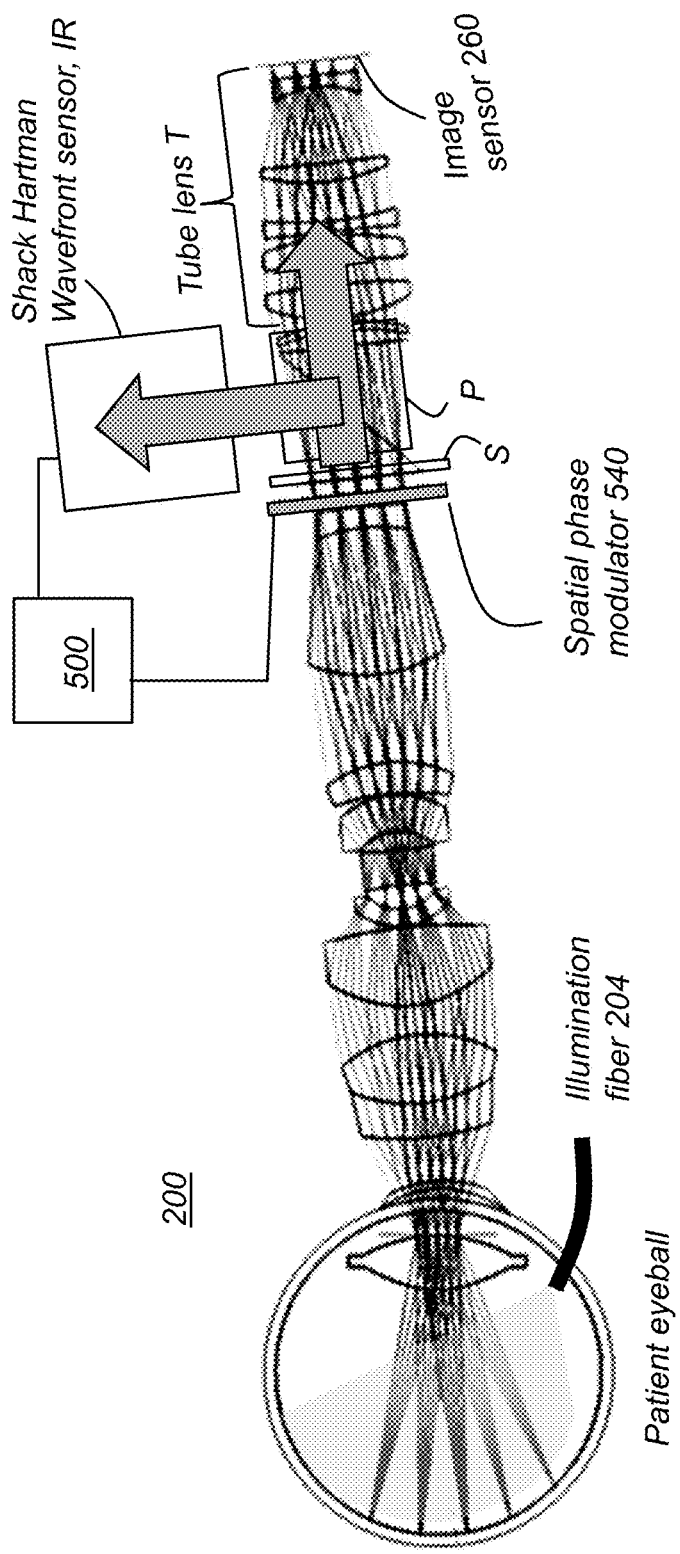
FIG. 17 is a schematic diagram that shows a system with connection to a Shack-Hartmann wavefront sensor and processor.

Adaptive optics can be added to the system using the input port. AO capabilities can help to provide correction where phase adjustment is needed, such as due to inhomogeneity in the vitreous fluid or in some other portion of the eye. A processor 500 can be included to sense wavefront information, such as from a Shack Hartman wavefront sensor, and to compensate for irregularities by controlling a spatial phase modulator 540, disposed adjacent to shutter S, at or near the image of the iris. FIG. 17 shows a system with connection to a Shack-Hartmann wavefront sensor and processor 500.

Contact Lens

Figure 18:
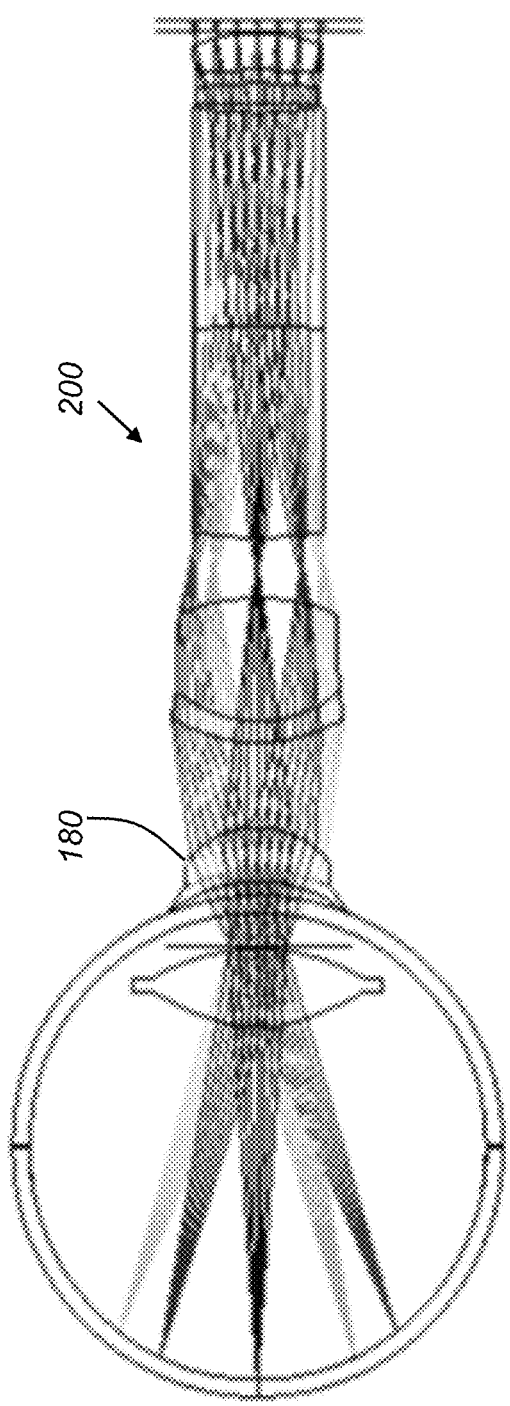
FIG. 18 shows use of a contact lens for imaging using an attachment for retinal imaging.

FIG. 18 shows use of a contact lens 180 for imaging using attachment 200. Use of contact lens 180 on the patient can help to reduce or eliminate cornea reflection during surgery. Contact lens 180 also allows for simpler optics in attachment 200. Relay 220 design is simplified when using contact lens 180; as a consequence, the relay assembly can be shortened. Cornea glare can be greatly reduced or eliminated. Contact lens 180 has a measure of compliance and can be connected to, or separated from, the attachment 200 optics.

Figure 19A:
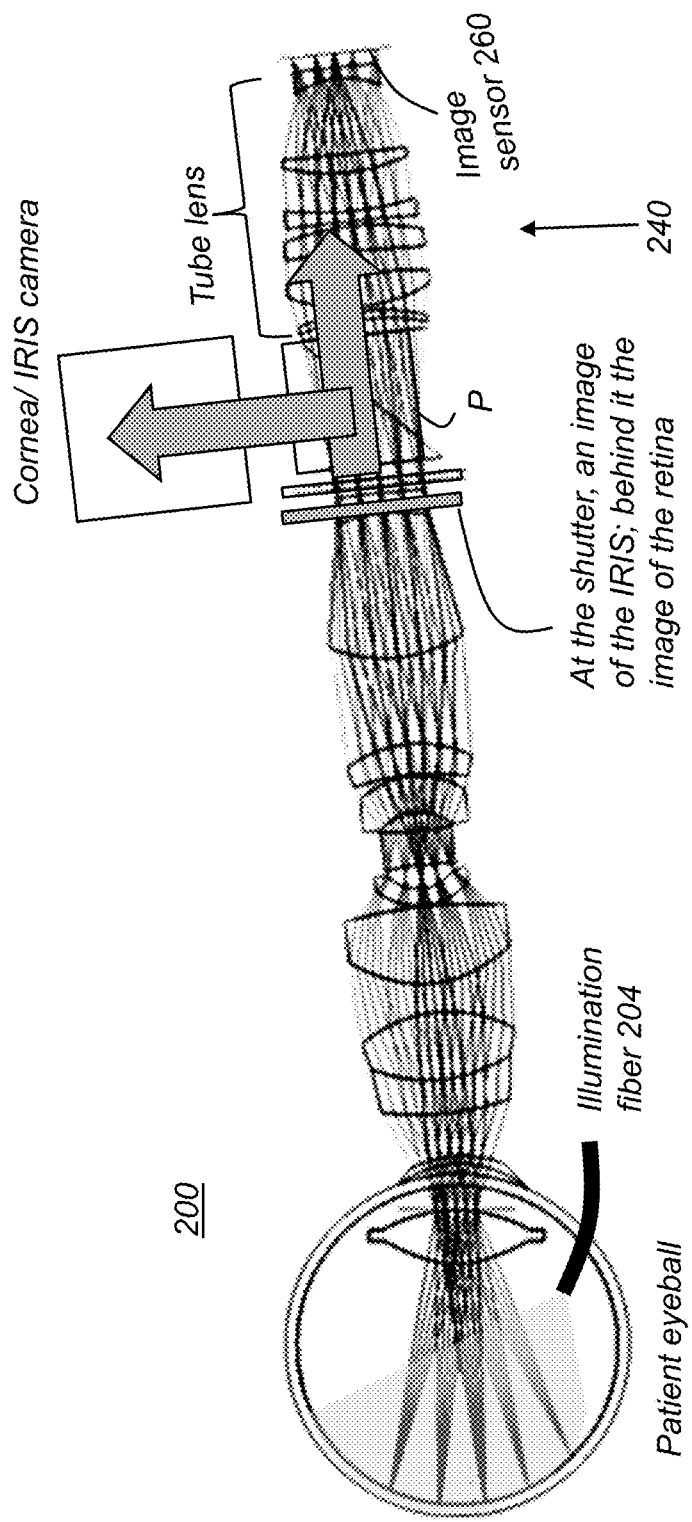
FIG. 19A is a schematic diagram that shows an optional connection to a cornea/iris camera.
Figure 19B:
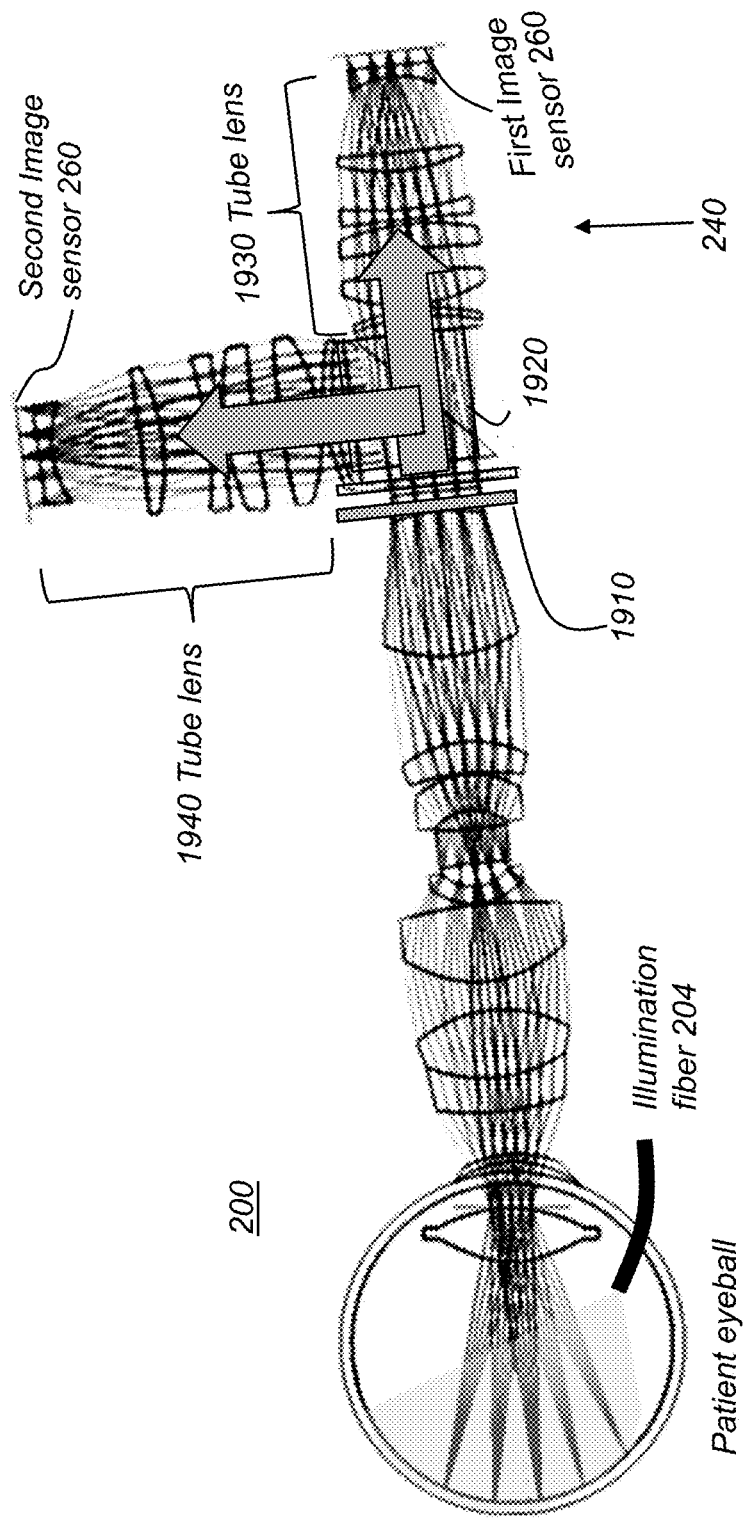
FIG. 19B is a schematic diagram that shows the optical connection for a two-channel dual sensor system.

FIG. 19A shows optional connection to a cornea/iris camera using shutter and input port subsystem 240. Alternately, or in concert with the above, as shown by FIG. 19B, the system can form 3D images using an additional external sensor. In this instance, the electronic shutter of FIG. 19A can be replaced by two fixed apertures 1910, each aperture 1910 having a corresponding polarizer, wherein the polarization states of the polarizers are orthogonal to each other, and wherein the beam splitter cube of FIG. 19A, is replaced by a polarizing beam splitter cube 1920 thereby directing a first optical channel to a tube lens 1930 and the first camera sensor 260; and directing the second optical channel to a second tube lens 1940 and second camera sensor 260.

Figure 19C:
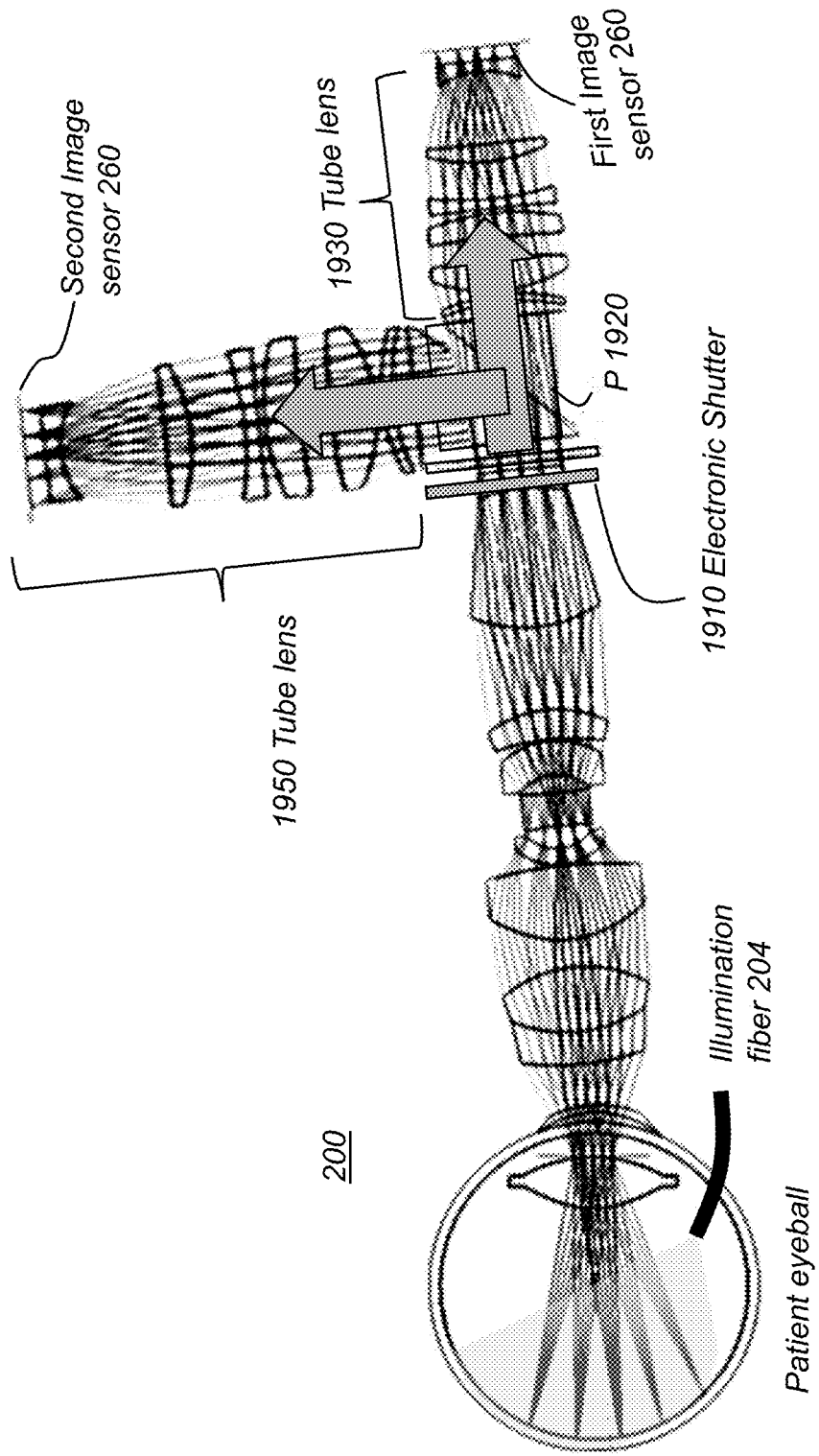
FIG. 19C is a schematic diagram that shows a two-sensor optical connection wherein the electronic shutter remains, however the tube lens to the first sensor is configured to image the retina, and the tube lens to the second sensor is configured to image the cornea.

In another embodiment, as shown in FIG. 19C, is a configuration wherein a two-sensor optical connection as in FIG. 19B is used, wherein the electronic shutter remains, however the tube lens 1950 to the first sensor of FIG. 19B is a different length to be configured to image the retina, while the second tube lens 1930 is configured to image the cornea simultaneously in 3D.

Figure 19D:
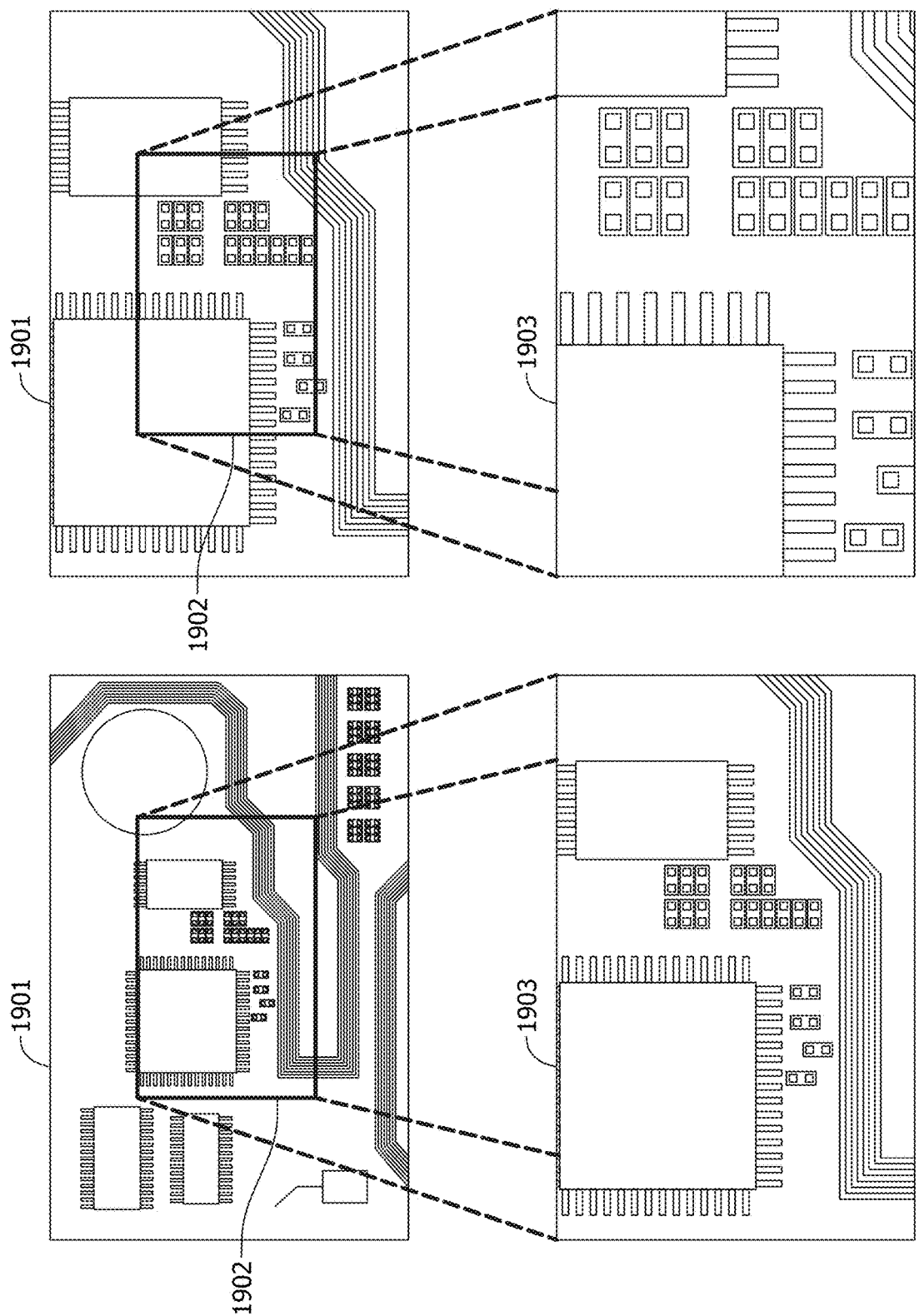
FIG. 19D depicts "digital zoom" which is a method of decreasing the precise angle of view of a digital photograph or video image by taking a subset of the pixels and digitally enlarging them.
Figure 19E:
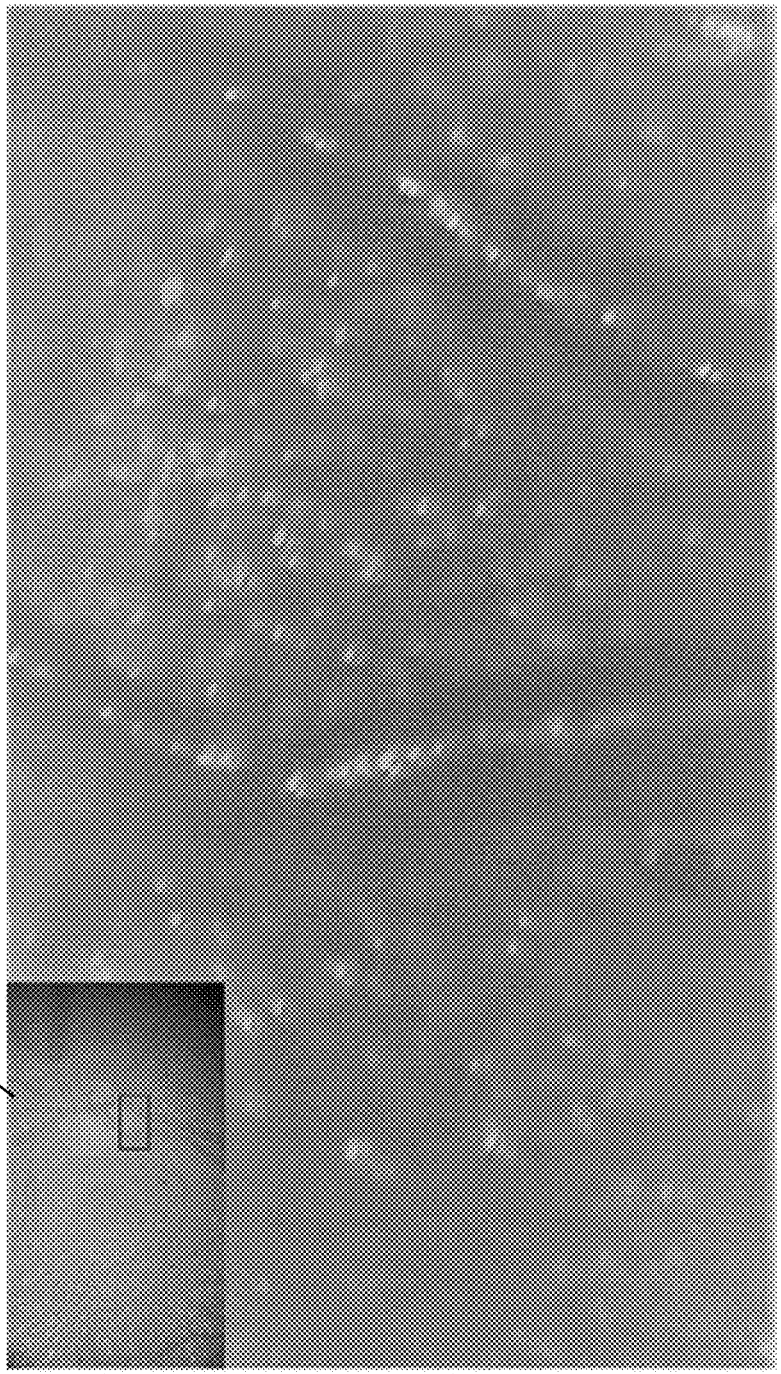
FIG. 19E depicts a picture-in-picture (PnP) feature of the digital microscopic device. When the surgeon begins to zoom in or magnify an image or area, an image of the larger area appears as a sub-image.
Figure 19F:
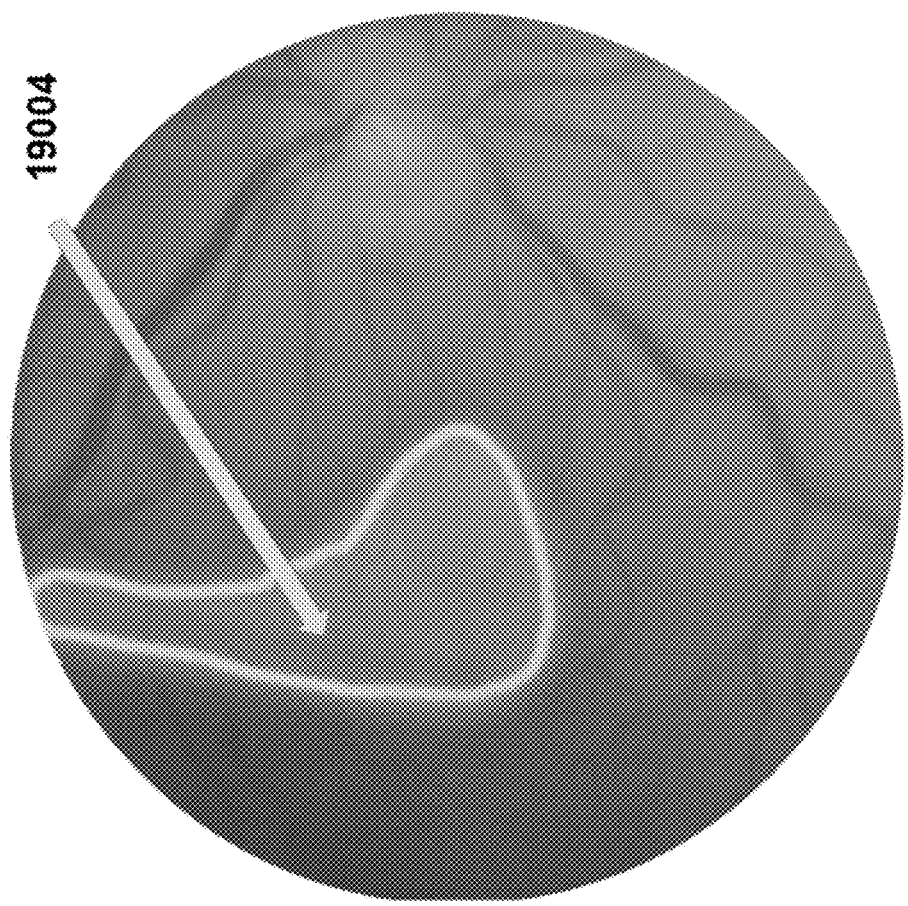
FIG. 19F depicts a picture-on-picture (PoP) imaging technique wherein an overlay of information is placed on the existing 2D or 3D image or video feed.

In another embodiment as shown in FIG. 19C, the retina could be displayed in full screen mode, while the anterior segment (including viscous) may be imaged and viewed in picture-in-picture mode as shown in FIG. 19E. In addition, one may transfer seamlessly between anterior mode to posterior mode for an eye examination or in surgery when going from a vitrectomy to an epiretinal membrane (EPM) peel. In another embodiment, as shown by FIG. 19F, the image captured by the sensor(s) may be magnified so that the surgeon can see details better. To accomplish the digital magnification, digital cropping using either the technique of FIG. 19A, or of 19B, can be used to provide digital zoom.

Referring to FIG. 19D by way of example, "digital zoom" is a method of decreasing the precise angle of view of a digital photograph or video image by taking a subset of the pixels. Digital zoom is accomplished by cropping a subset of the pixels from the original image 1901 while keeping the same aspect ratio on the subset image 1902 as the original and then scaling the subset image 1902 back up to the original dimensions of the original image 1901. These processes can be repeated until the resolution is so low that the image quality does not justify further digital zoom magnification, which would be when the cropped and enlarged image reaches the same pixel size as exist in the sensor(s). This typically occurs when the same resolution exists in the cropped and enlarged image as is extant in the display(s) used, as in image 1903. For example, it is when the final cropped and enlarged image is 4K (3,840×2,160 at 16:9 aspect ratio) and so is the display(s).

FIG. 19E depicts a picture-in-picture (PnP) feature of the device. When the surgeon begins to zoom in or magnify an image or area, the controller may be prompted to begin forming an image-within-image, or a picture-in-picture, which may appear as an image 19001 in the corner of the larger magnified image 19002, while the larger picture is the actual magnified image 19002. The PnP may allow the viewer to keep their orientation and understand where they are located within the whole image so as not to lose orientation to the larger structure.

This utility is designed to simplify identifying where the viewer is (i.e., in an area of the retina) in relation to the non-zoomed image. This feature may permit the surgeon to examine the same region of the image with different zoom levels or different angles, with respect to the whole image before it was magnified.

Through software and the controller, each image may be a dynamically linked map that follows along the same coordinates. Changing the coordinates of the center on one of them may lead to an automatic displacement of the center in the same point of the second, and a coordinate display unit informs of the current coordinates. Thus, when a user begins to magnify or zoom in on an image or video, a secondary rendering of the image may appear on the lens of the viewport, and the larger, magnified image may become the primary image.

The primary image may be magnified as specified by the user, while the secondary image may capture the original coordinates of the primary image before it was magnified. Through software control and menu selection, the secondary image can be pinned to either the top left corner, top right corner, bottom left corner, or bottom right corner depending on the surgeon's preference, or as a preset, and can be shifted to a new location using touch commands on the internal display, which may be a touch screen, or by other control.

The secondary image may be a digitally altered subsampling of the primary image. Thus, the secondary image may fill the viewport showing an inspector their region of interest, while the primary image may be placed in a corner of the viewport to serve as a map. The position of the secondary image may then be indicated on the primary image via an overlay, whether varying capacity monochrome or color. Digital altering of the primary image can include digital zooming, color contrast enhancement, color picking, or other video processing system that is useful for the surgeon.

The system computing and controller can also present imaging or video in "Picture-in-Picture" technology in the microscope instrument which may permit a surgeon or user of any of the 3D displays mentioned herein to watch two images or videos (primary and secondary) simultaneously. Thus, the surgeon could simultaneously see imaging from two separately images. The primary image may fill the entire screen or projection across a display, while the secondary image may be a smaller (approx. ¼th of the primary image size), floating window pinned to a corner of the screen (always on top of all other windows), which may allow users to keep an eye on what is happening in both images at one time. This may be especially helpful if the surgery is near or adjacent to an especially vulnerable organ. Thus, the surgeon could see the (larger) image of the cutting, ablation, or resecting, watching from another angle to how close the instrument is to a vital or vulnerable organ.

In addition, to reduce the signal noise so that the quality of the image remains as sharp as the original, pixel-binning may be used. Pixel-binning is a process where a clocking scheme is used to combine the charge (light) collected by several adjacent pixels to reduce the "noise". Noise in this instance is a random variation of brightness or color information in images and is usually an aspect of electronic noise which is created by the digital camera sensors. To correct for this "noise" upon digital magnification, pixel-binning can be used whereby the viewer can obtain the best detail in good lighting conditions, while also being able to produce high-quality low-light shots. The high-quality low-light video or images is created by sampling multiple pixel's light. The sensor or sensors chosen for the microscope contain the largest pixel size possible or available. Thus, the larger a sensor's pixels (or photosites), the greater the light-gathering ability, which is axiomatic. However, it can take a significant number of pixels to render images in high resolution. The size of a photosite is called the pixels' "pixel pitch", which is measured in microns. Thus, a larger micron pixel has a higher pixel pitch. Because not all photosites collect the same amount of light (red, green, and blue) pixel-binning is used to sum the signals of adjacent pixels to enhance the resolution and increase the signal-to-noise ratio. The resolution is enhanced because the higher the signal to noise ratio, the clear the definition is and the more the boundaries between different color and brightness of the pixels is evident. Thus, the combination of digital zoom and pixel-binning permits the zoom feature to go far beyond what optical zoom alone can do. This is one of the major benefits of having digital zoom.

As shown in FIG. 19F, another capability of the system is to create picture-on-picture (PoP) images where an existing video feed 19003 has a digital overlay 19004 of pre-designated or real-time generated by the computer controller origin is added to an existing 2D or 3D video or still shot surgery feed. The advantage of this setup is that, the system can take the signal and render image content overlayed in multiple display medias, in a connected telemedicine method, including displaying the video remotely in the instance of expert-assisted surgery, where addition video, imagery or test is overlayed on the existing video feed. Thus, a remote surgeon, team, or another viewer could visualize the internals captured by the cameras and assist the surgeon physically onsite with information, advice, instruction, or caution by touch or 6 DoF (degrees-of-freedom) sensing to show a market overlayed on the surgery video feed. Picture-over-picture is a method in which any number of image classification and bounding techniques may be used by the computer system to understand the importance of an object in the field. This can be achieved by using high color depth sensors to better determine objects that are minimally viewable.

On PoP, when a bounding area is defined on the video containing that object, the computer system may then use edge detection, and other computer vision techniques to highlight the specific region of interest in the video. This highlighted portion is the overlaid-on top of the video as captured by the camera sensors at the point of the computer system so that the picture-over-picture image is displayed to the viewer on the monitor, etc.

Figure 20:
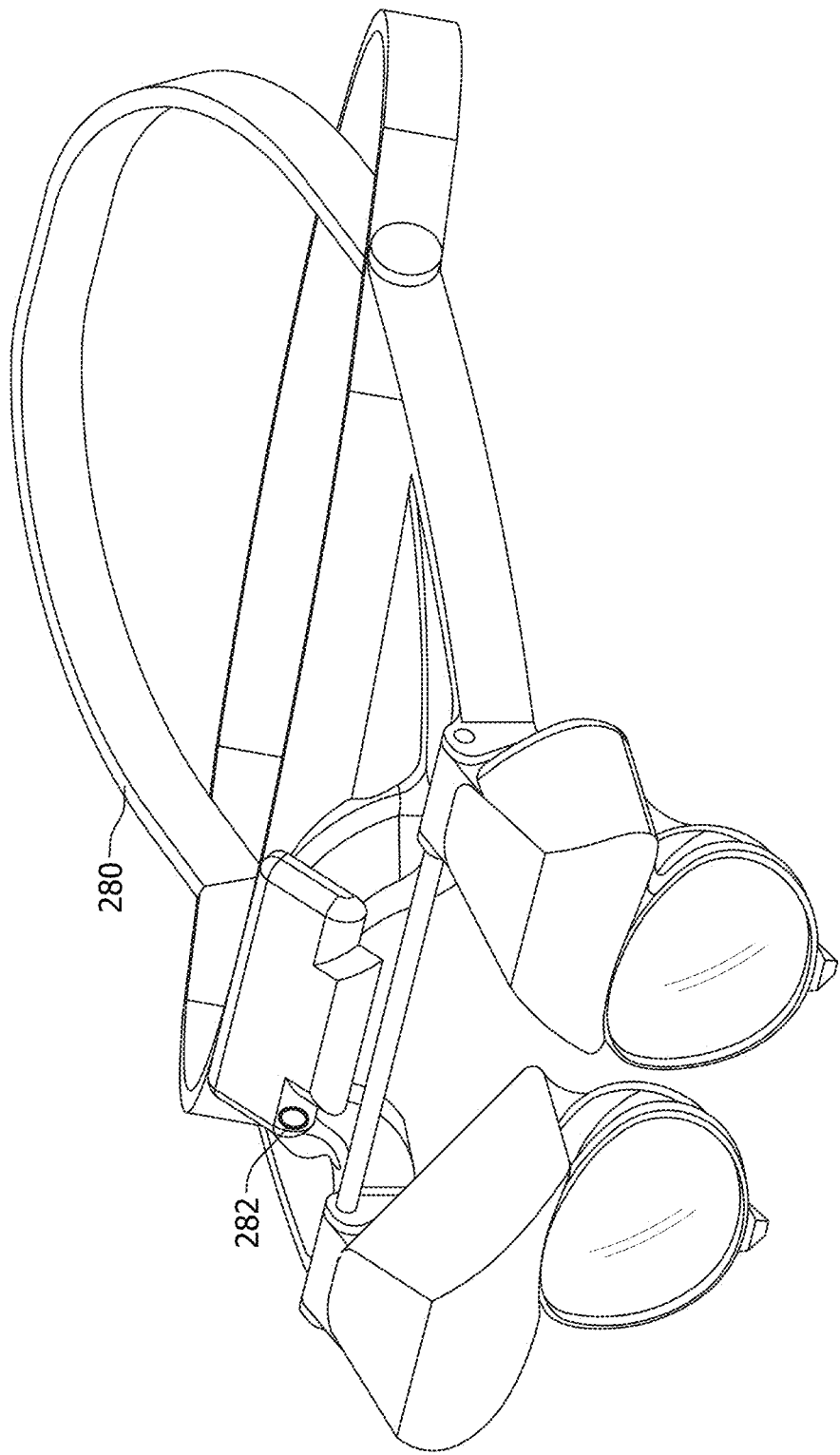
FIG. 20 shows an AR headset for viewing images of the cornea and related features.
Figure 21:
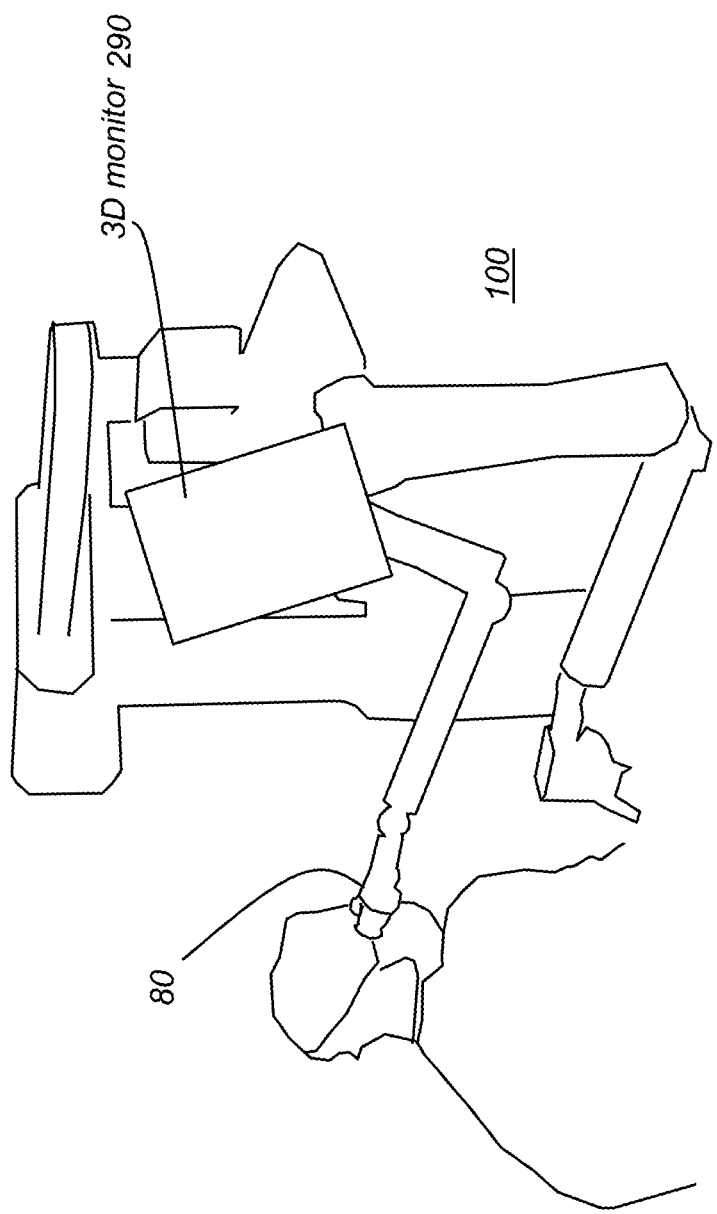
FIG. 21 shows a 3D monitor.

Alternatively, the 2D or 3D image created by the camera or image sensors can be transmitted in wired or wireless form to an imager such as an AR/XR wireless headset 280, as shown in FIG. 20, or to a 3D monitor 290, which could be an 3D "glasses free" autostereoscopic monitor as shown in FIG. 21. Headset 280 can include cameras and other sensors 282 for obtaining viewer instructions from the surgeon or other practitioner. Extended reality (XR) viewing can also be provided, including Mixed Reality (MR), and Virtual Reality (VR). Headset 280 can include micro-displays, head tracking, eye-tracking, and depth-sensor cameras to display images to the wearer, effectively creating the illusion of augmented reality. Monitor 290 can also provide an operator interface for making viewer adjustments, such as for configuring aperture dimensions, spacing, or azimuth angles, as described previously.

FIG. 21 shows an autostereoscopic 3D monitor 290 of the present disclosure that provides 4Kvideo and 3D Holographic image output for the patient cornea using a stereomicroscope apparatus 100. Display presentation can be with or without polarized 3D glasses or shutter glasses. Image presentation is at high resolution and suitably positioned for viewing by the surgeon, without requiring turning of the head for a surgeon and others on an operating room team. Viewing optics 80 can track viewer position.

Figure 22:
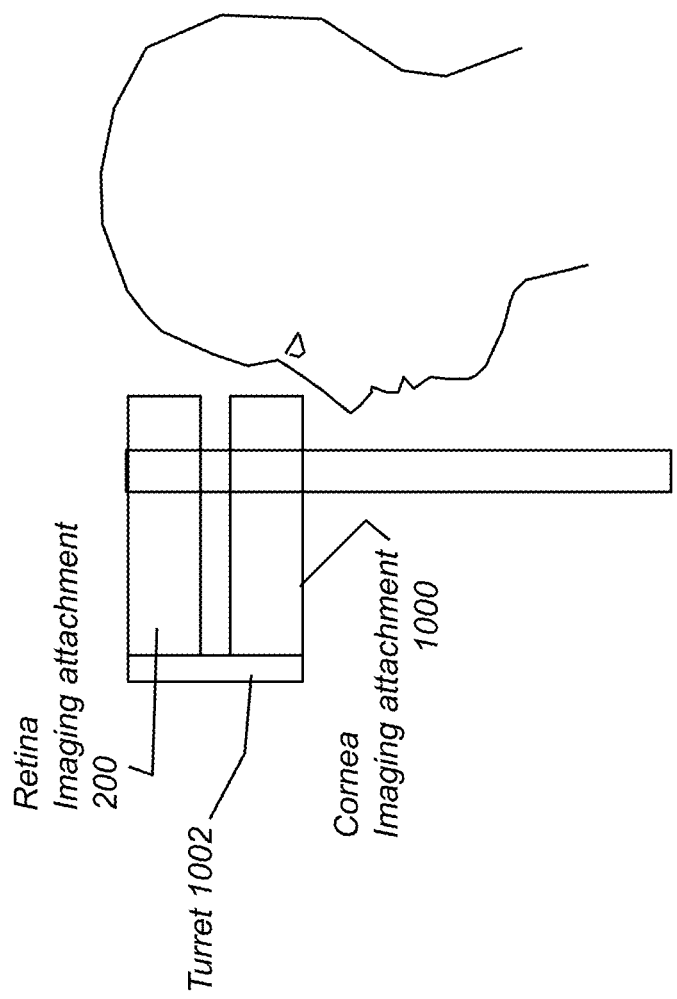
FIG. 22 shows use of cornea and retina imaging attachments in a turret arrangement.

The system can be used in combination with a cornea imaging system 1000 such as is shown in FIG. 22. The system may use a combination of elements, or two systems mounted adjacently on a microscope turret 1002, as shown in FIG. 22. The retina imaging attachment described herein can be used as a standalone imaging device, typically useful for office examination by the practitioner. When mounted as part of a larger imaging system, the retina imaging attachment can be mounted in the turret of FIG. 22 or other type of switching device and used to automate office examination imaging as well as for imaging during surgical procedures. Robotic actuators, not shown, can be used to position and increment the imaging attachment at different angles for more complete imaging content.

Tables 1 and 2 give exemplary design data for optical features of a retina imaging attachment according to an embodiment of the present disclosure. The full FOV is 50 degrees. Entrance pupil diameter is 3 mm. The system is corrected over the visible range.

Figure 23:
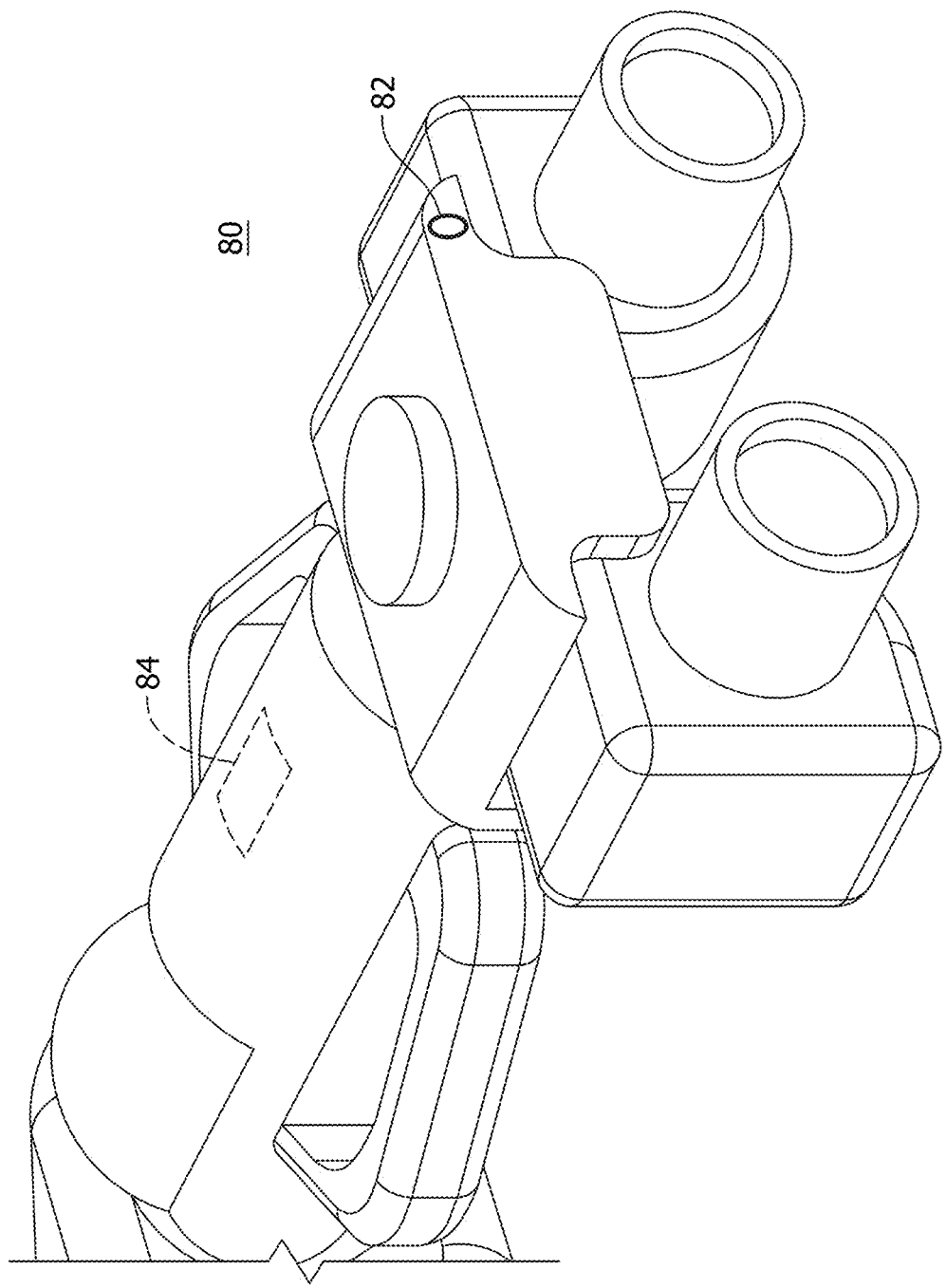
FIG. 23 is a perspective view that shows microscope viewing optics 80 that can be used for visualization with the stereomicroscope apparatus.

FIG. 23 is a perspective view that shows microscope viewing optics 80 that can be used for visualization with the stereomicroscope apparatus. Each eye piece can have high resolution, such as 4K resolution with full color 3D imaging, from the digital surgery feed. Sensors 82 in viewing optics 80 are used to sense surgeon position, allowing actuators 84, such as motors and associated components, to extend the viewing optics 80 to reach out for the surgeon's head/eyes and stop just short of the surgeon's position. Sensors 82 can include cameras or infrared sensors, for example. This enables the surgeon to change positions during surgery, while viewing optics 80 follow the surgeon's posture without the need for manual adjustment or touch.

Voice plus Eye-Tracking redundancy for the various display options can help to provide the surgeon with control of tools using gaze tracking or audible commands, for hands-free operation.

Whereas, the devices and methods have been described in relation to the drawings and claims, it should be understood that other and further modifications, apart from those shown or suggested herein, may be made within the spirit and scope of this disclosure.

The apparatus of the present disclosure has been described in detail with particular reference to a presently preferred embodiment, but it will be understood that variations and modifications can be effected within the spirit and scope of the disclosure. The presently disclosed embodiments are therefore considered in all respects to be illustrative and not restrictive. The scope of the invention is indicated by any appended claims, and all changes that come within the meaning and range of equivalents thereof are intended to be embraced therein.

TABLE 1

Design data for retina attachment

| Surf | Type | Radius | Thickness | Glass | Note |
|---|---|---|---|---|---|
| OBJ | STANDARD | Infinity | Infinity | | |
| STO | STANDARD | Infinity | 3.58 | | 1 |
| 2 | EVENASPH | 25.675 | 0.40 | 808227 | |
| 3 | STANDARD | 7.869 | 6.25 | 528764 | |
| 4 | STANDARD | −6.081 | 2.23 | | |
| 5 | EVENASPH | 6.893 | 3.05 | 808227 | |
| 6 | STANDARD | −32.332 | 0.10 | | |
| 7 | STANDARD | 5.926 | 2.17 | 103180 | |
| 8 | STANDARD | 3.057 | 1.65 | | |
| 9 | STANDARD | −12.662 | 0.52 | 595392 | |
| 10 | STANDARD | Infinity | 0.33 | 595392 | 2 |
| 11 | STANDARD | 11.684 | 2.00 | | |
| 12 | STANDARD | −2.929 | 1.55 | 850322 | |
| 13 | STANDARD | −4.993 | 0.12 | | |
| 14 | STANDARD | −15.104 | 2.41 | 743493 | |
| 15 | EVENASPH | −6.334 | 5.18 | | |
| 16 | STANDARD | 8.600 | 9.17 | 595677 | |
| 17 | STANDARD | −15.157 | 0.44 | 784257 | |
| 18 | EVENASPH | −1188.487 | 0.50 | | |
| 19 | STANDARD | Infinity | 8.00 | 540594 | 3 |
| 20 | STANDARD | Infinity | 0.10 | | |
| 21 | STANDARD | Infinity | 0.50 | 516641 | 4 |
| 22 | STANDARD | Infinity | 3.94 | | |
| 23 | EVENASPH | −16.154 | 4.75 | 623581 | |
| 24 | STANDARD | −8.357 | 1.63 | | |
| 25 | STANDARD | 79.745 | 2.30 | 834427 | |
| 26 | EVENASPH | −19.368 | 0.28 | | |
| 27 | STANDARD | 114.521 | 0.70 | 648530 | |
| 28 | STANDARD | −44.389 | 0.29 | | |
| 29 | STANDARD | −146.641 | 0.60 | 922188 | |
| 30 | STANDARD | 28.227 | 0.95 | | |
| 31 | EVENASPH | 27.937 | 8.75 | 804465 | |
| 32 | STANDARD | 192.361 | 3.98 | | |
| 33 | STANDARD | −6.519 | 0.57 | 567428 | 5 |
| 34 | STANDARD | Infinity | 1.00 | | |
| Sensor | STANDARD | Infinity | | | |

Notes to Table 1:
1. Eye
2. Intermediate image
3. Prism
4. Shutter/stop
5. Field lens

TABLE 2

Aspheric Coefficients for retina attachment surfaces

| Coeff. | 2 | 5 | 15 | 18 | 23 | 26 | 31 |
|---|---|---|---|---|---|---|---|
| A4 | −6.26E−04 | −5.07E−04 | −9.74E−05 | 4.55E−04 | −7.51E−04 | −4.14E−04 | −8.23E−05 |
| A6 | −3.56E−05 | −4.82E−07 | −2.27E−07 | 4.99E−06 | −6.26E−06 | 5.89E−06 | 4.77E−06 |
| A8 | 1.92E−06 | −5.11E−07 | −2.75E−07 | 1.18E−07 | −2.00E−07 | −6.19E−08 | −7.93E−08 |

TABLE 2-continued

Aspheric Coefficients for retina attachment surfaces

| Coeff. | 2 | 5 | 15 | 18 | 23 | 26 | 31 |
|---|---|---|---|---|---|---|---|
| A10 | −3.54E−08 | 1.59E−08 | 1.30E−08 | 1.34E−09 | 4.24E−09 | 1.69E−09 | 4.33E−09 |
| A12 | −1.93E−10 | −2.09E−10 | −4.15E−10 | 4.35E−11 | 0.00E+00 | 0.00E+00 | 0.00E+00 |

The invention claimed is:

1. An apparatus for obtaining an image of an eye comprising:
   (a) an optical relay that defines a first optical path and is configured to relay an image of an iris of the eye along the first optical path to a pupil;
   (b) a shutter disposed at the pupil and configured to define at least a first shutter aperture for control of light transmission through the pupil position;
   (c) a tube lens disposed to direct light from the shutter aperture to an image sensor; and
   (d) a prismatic input port disposed between the shutter and the tube lens and configured to combine the first optical path with a second optical path.

2. The apparatus of claim 1 wherein the second optical path at the input port is orthogonal to the first optical path.

3. The apparatus of claim 1 wherein the second optical path conveys a light signal outside the visible spectrum that extends from 380-750 nm.

4. The apparatus of claim 1 wherein the shutter is configured to define the first shutter aperture for a left-eye image and to define a second shutter aperture for a right-eye image.

5. The apparatus of claim 4 wherein the first and second shutter apertures are disposed horizontally side-by-side.

6. The apparatus of claim 4 wherein spacing between the first and second shutter apertures is variable.

7. The apparatus of claim 1 wherein the apparatus is configured for obtaining an image of a retina.

8. The apparatus of claim 4 wherein the shutter is configured to adjust an azimuth angle defined from center to center of the first and second shutter apertures according to a signal from a system processor.

9. The apparatus of claim 4 wherein the first and second shutter apertures are elliptical.

10. The apparatus of claim 1 further comprising an afocal optical relay formed by a concave primary mirror and a convex secondary mirror and configured to direct light over a scanner path to and from the eye.

11. The apparatus of claim 10 wherein the afocal optical relay images a scanner onto the pupil of the optical relay.

12. The apparatus of claim 10 wherein the light directed from the afocal optical relay is a sample beam for an optical coherence tomography apparatus.

13. The apparatus of claim 1 further comprising an actuator coupled to the image sensor and energizable to adjust an axial position of the image sensor for light-field imaging.

14. The apparatus of claim 1 further comprising a phase modulator disposed at the image of the iris.

15. An apparatus for obtaining an image of a retina comprising:
   (a) an optical relay that defines an optical path and is configured to relay an image of the iris along the optical path to a pupil;
   (b) a shutter element disposed at the pupil and configured to form a first aperture and a second aperture for control of light transmission through the pupil position;
   (c) a first camera disposed to acquire light conveyed through the first aperture for a left eye of the viewer; and
   (d) a second camera disposed to acquire light conveyed through the second aperture for a right eye of the viewer.

16. The apparatus of claim 15 further comprising a prismatic input port disposed between the optical relay and a tube lens and configured to combine, onto the optical path, light from the optical relay with light conveyed along a second light path that is orthogonal to the optical path at the input port.

17. The apparatus of claim 16 wherein the light along the second path comprises a sample signal for an optical coherence tomography apparatus.

18. The apparatus of claim 16 further comprising an afocal optical relay formed by a concave primary mirror and a convex secondary mirror and configured to direct light from a scanner to and from the retina through the prismatic input port.

19. A method for stereoscopic imaging of a patient's retina by a viewer comprising:
   (a) relaying an image of the patient's iris to a shutter that is configured to provide a left-eye aperture and a right-eye aperture for the viewer, wherein the left-eye aperture and right-eye aperture convey light from different portions of a field of view that includes the patient's retina;
   (b) forming the left- and right-eye apertures in an alternating timing sequence;
   (c) capturing image content from light conveyed through the left- and right-eye apertures; and
   (d) rendering a stereoscopic image to the viewer according to the captured image content.

20. The method of claim 19 further comprising adjusting for inter-pupil distance of the viewer by shifting the spatial positions of the left- and right-eye apertures relative to the field of view.

21. The method of claim 19 further comprising forming a single aperture for viewing by the viewer.

22. The method of claim 19 further comprising avoiding obstacles to patient vision by shifting the spatial positions of the left- and right-eye apertures relative to the field of view.

23. The method of claim 19 wherein shifting the relative spatial positions alters a horizontal azimuth for viewing the retina.

* * * * *